United States Patent [19]
Kashihara et al.

[11] Patent Number: 5,739,347
[45] Date of Patent: Apr. 14, 1998

[54] OPTICALLY ACTIVE β-AMINOALKOXYBORANE COMPLEX

[75] Inventors: Hiroshi Kashihara; Mikio Suzuki; Yoshio Ohara, all of Funabashi, Japan

[73] Assignee: Nissan Chemical Industries Ltd., Tokyo, Japan

[21] Appl. No.: 848,173

[22] Filed: Apr. 29, 1997

Related U.S. Application Data

[62] Division of Ser. No. 481,505, filed as PCT/JP94/00056, Pat. No. 5,663,348.

Foreign Application Priority Data

Jan. 20, 1993 [JP] Japan ............................ 5-7827
Mar. 25, 1993 [JP] Japan ............................ 5-66825

[51] Int. Cl.[6] ................ C07D 263/14; C07D 263/60
[52] U.S. Cl. .................................. 548/215; 548/217
[58] Field of Search ............................ 548/215, 217

[56] References Cited

U.S. PATENT DOCUMENTS

| | | |
|---|---|---|
| 4,897,490 | 1/1990 | Sit et al. |
| 5,412,099 | 5/1995 | Goldmann et al. ........... 548/180 |
| 5,663,348 | 9/1997 | Kashihara ..................... 546/173 |

FOREIGN PATENT DOCUMENTS

| | | |
|---|---|---|
| 772624 | 11/1967 | Canada. |
| 0 171 175 A1 | 2/1986 | European Pat. Off. |
| 0 453 288 A1 | 10/1991 | European Pat. Off. |

OTHER PUBLICATIONS

T. R. Govindachari et al., "Chemical Examination of *Tylophora Astmatica–IV*[1] Synthesis of Tylophorine[2]", Tetrahedron, vol. 14, pp. 284–287, 1961.

B. Chauncy et al., "Synthesis of Phenanthroindolizidines. II Synthesis of (+-)-Tylocrebine, (+-)-Tylophorine, (+-)-Antofine, and (+-)-2,3-Dinethoxyphenanthroindolizidine", Chemical Abstracts, Abstract No. 13313g, vol. 74, No. 3, 18 Jan. 1971.

B. Chauncy et al., "Synthesis of Phenanthroindolizidine", Chemical Abstracts, Abstract No. 88024q, vol. 70, No. 19, 12 May 1969.

H. Hashizume et al., "Resolution of D,L–Pantolactone", Chemical Abstracts, Abstract No. 38872p, vol. 110, No. 5, 30 Jan. 1989.

E. J. Corey et al., "Enantioselective Route to a Key Intermediate in the Total Synthesis of Ginkogolide B", Tetrahedron Letters, vol. 29, No. 26, pp. 3201–3204, 1988.

Takeshi Hanamoto et al., "A Facile Entry to β, δ–Diketo and Syn–β,δ–Dihydroxy Esters", Tetrahedron Letters, vol. 29, No. 49, pp. 6467–6470, 1988.

M. Cegla, "Chiral N–(Arylalkyl)–2–Amino–1–Butanol Derivatives as Stereoselective Reduction Agents of Ketones", Chemical Abstracts, Abstract No. 39327q, vol. 107, No. 5, 3 Aug. 1987.

Chemical Abstracts, vol. 70, Jul. 23, 1969, p. 368, AN–88024q.

Chemical Abstracts, vol. 74, Feb. 23, 1971, p. 326, AN–13313g.

Chemical Abstracts, vol. 107, Aug. 13, 1987, AN–39327q.

Chemical Abstracts, vol. 110, Feb. 17, 1989, AN38872p.

Tetrahedron, vol. 14, 1961, pp. 284–297, T.R. Govindachari et al., "Chemical Examination of Tylophora Asthmatica–IV".

Aust. J. Chem., vol. 22, p0p. 427–429, 1969, B. Chauncy et al., "A New Synthesis of Phenanthoindolizidine".

Aust. J. Chem., vol. 23, pp. 2503–2516, 1970, B. Chauncy et al., "Synthesis of Phenanthroindolizidines".

*Primary Examiner*—Johann Richter
*Assistant Examiner*—Ebenezer Sacley
*Attorney, Agent, or Firm*—Oblon, Spivak, McClelland, Maier & Neustadt, P.C.

[57] ABSTRACT

An optically active β-aminoalkoxyborane complex of the formula (I):

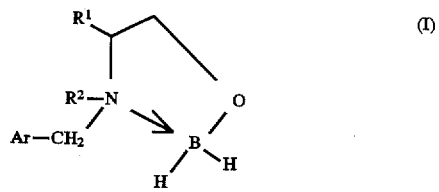

wherein $R^1$ is $C_1$–$C_8$ alkyl, $C_3$–$C_7$ cycloalkyl, $C_7$–$C_{11}$ aralkyl or $C_6$–$C_{10}$ aryl, $R^2$ is hydrogen, $C_1$–$C_8$ alkyl, $C_3$–$C_7$ cycloalkyl or $C_7$–$C_{11}$ aralkyl, or $R^1$ and $R^2$ together form $(CH_2)_n$ wherein n is 3 or 4, and Ar is naphthyl, anthryl or phenanthryl, which may be substituted by from 1 to 3 substituents selected from the group consisting of halogen, nitro, $C_1$–$C_6$ alkyl, $C_3$–$C_7$ cycloalkyl, $C_2$–$C_6$ alkenyl, $C_2$–$C_6$ alkynyl, $C_7$–$C_{11}$ aralkyl, $C_6$–$C_{10}$ aryl, $C_1$–$C_6$ alkoxy and styrene polymer substituents.

1 Claim, No Drawings

OPTICALLY ACTIVE β-AMINOALKOXYBORANE COMPLEX

This is a Division of application Ser. No. 08/481,505 filed on Jul. 19, 1995, now U.S. Pat No. 5,663,348 which was filed as International application Ser. No. PCT/JP94/00056 on Jan. 17, 1994.

TECHNICAL FIELD

The present invention relates to a novel optically active β-aminoalkoxyborane complex and a process for producing an optically active alcohol, wherein the complex is applied as a reducing agent to a carbonyl compound. Particularly, it relates to a process for producing an optically active 1,3-syn-diol compound wherein this borane complex is applied to a 1,3-dicarbonyl compound.

BACKGROUND ART

Many physiologically active substances for pharmaceuticals, agricultural chemicals or cosmetics have a 1,2- or 1,3-syn-diol structure. For example, a series of HMG-CoA reductase inhibitors as one type of antihyperlipemia agents have a 1,3-syn-diol as a common partial structure at their mevalonic acid chain moieties, which constitutes an essential structure for developing the reductase inhibitory activities.

Further, among natural physiologically active substances, there are many substances which have a 1,3-syn-diol structure. For example, prostaglandin F1α and F2α having oxytocic activities or vasopressor activities, pentamycine which is a polyene macrolide antibiotic, amphotericine B which is a polyene-type antimycotic, misaquinolide A which is an antitumor macrolide, G-strophatine which is a cardiac glycoside and pulkerine which is a sesquiterpene contained in an Indian blanket (*Gaillardia pulchella*) may be mentioned.

Heretofore, various methods for preparing this 1,3-syn-diol have been developed by means of chemical techniques (Tetrahedron Lett., 28, 155 (1987), Tetrahedron Lett., 26, 2951 (1985)). However, these methods require many steps, since a first chiral center is introduced and a second chiral center is constructed based on the first chiral center, and it requires an extremely low temperature as a reaction condition to obtain the desired 1,3-syn-diol in high optical yield and at a high syn-selectivity. Thus, they had many industrial limitations.

Heretofore, a number of methods have been known for producing an optically active alcohol compound by asymmetrically reducing a carbonyl compound by means of an optically active reagent. Namely, many methods including, for example, a method by Corey et al. employing an optically active borane complex (E. J. Corey and A. V. Gavai, Tetrahedron Lett., 29, 3201 (1988)), a Meerwein-Ponndolf-Verley (MPV) type asymmetric reduction method (M. M. Midland, D.C. McDowell and Gabriel, J. Org. Chem., 54, 159 (1989)) and a method employing an enzyme or a microorganism (G. Frater, Helv. Chim. Acta, 62, 2815, 2829 (1979) may be mentioned.

For asymmetric reduction of aromatic carbonyl compounds, many reagents showing high selectivity have been developed. However, it has been considered difficult to attain high selectivity for asymmetric reduction of a dialkylcarbonyl even by using these reagents, and it has been possible to attain an asymmetric yield of only 50% ee at best. Generally, high-electrons of unsaturated groups of aromatic carbonyl compounds are considered to provide substantial effects in a transition state for asymmetric reduction, and for a dialkylcarbonyl with which no such substantial electronic effects can be expected, a reagent is required to have an ability of recognizing the difference in steric effects (Organic Synthetic Chemistry, Vol. 45, No. 2, p. 101 (1987)). Accordingly, in the case of a substrate such as 2-hexanone, no reducing reagent which is capable of sufficiently providing such an ability, has been known. The above-mentioned reagents for asymmetric reduction are all used for asymmetric reduction of monocarbonyl compounds only, and little applications to dicarbonyl compounds have been known.

On the other hand, a method by Yamazaki et al. employing an optically active borane complex is known (Japanese Unexamined Patent Publication No. 146786/1982). Namely, this method is directed to asymmetric reduction of acetophenones by means of an optically active borane complex prepared from (S)-1-benzyl-2-pyrrolidine methanol and borane. However, the optical purity thereby attainable is only at a level of 69% at the maximum, and it takes a long time of about 60 hours. Thus, this method can hardly be regarded as a practical method. Itsuno et al. have tried asymmetric reduction of a carbonyl compound by a borane complex having a styrene polymer introduced to the benzyl moiety of this (S)-1-benzyl-2-pyrrolidine methanol (S. Itsuno, K. Ito, T. Maruyama, A. Hirao and S. Nakahama, Bul. Chem. Soc. Jpn., 59, 3329 (1986)), but have failed to attain a satisfactory optical purity. Both the Yamazaki et al. method and the Itsuno et al. method have been used for reduction of monocarbonyl compounds and have not been utilized for reduction of dicarbonyl compounds. As an application to dicarbonyl compounds, a method by Noyori et al. employing a BINAP-Ru complex (Ryoji Noyori and Hidemasa Takaya, Chemistry, 43, 146 (1988) and R. Noyori, Chem. Soc. Rev., 18, 187 (1988)) is known, and this method is applied also to direct reduction of 1,2-dicarbonyl and 1,3-dicarbonyl compounds. In any case, however, the resulting optically active diols are of anti-form.

According to a recent method by Hiyama et al. for direct asymmetric reduction of 1,3-dicarbonyl compounds having asymmetric ester groups introduced thereto (European Patent No. 475627) or an asymmetric reduction method of 1,3-dicarbonyl compounds employing an optically active borane reagent (Tetrahedron Lett., 29, 6467 (1988)), 1,3-syn-diol compounds are obtainable by the intended syn-selective asymmetric reduction, but no adequate results have been obtained with respect to the asymmetric yield. Thus, a process for direct reduction of dicarbonyl compounds to obtain optically active syn-diol compounds, has not yet been established.

DISCLOSURE OF INVENTION

It is an object of the present invention to obtain an optically active alcohol in good asymmetric yield by asymmetric reduction of a carbonyl compound, particularly to obtain an optically active 1,3-syn-diol compound in good asymmetric yield at a high syn-forming rate by simultaneously reducing two carbonyl groups of a dicarbonyl compound, and to provide an excellent reducing catalyst capable of realizing the object and to provide an optically active 1,3-syn-diol compound by using such a catalyst.

The present inventors have conducted extensive studies with an aim to develop a reducing reagent capable of providing a high asymmetric yield and a high syn-selectivity and useful under a wide range of reaction conditions and a process for producing an optically active 1,3-syn-diol compound, and as a result, have found it possible to produce an optically active 1,3-syn-diol compound in the maximum asymmetric yield of 100% ee and at a high syn-selectivity of 99% by reducing a 1,3-dicarbonyl compound by means of an optically active β-(N-naphthylmethyl)aminoalkoxyborane complex prepared from an optically active β-(N-naphthylmethyl)aminoalcohol compound and borane. The present-invention has been accomplished on the basis of this discovery.

Thus, the present invention provides an optically active β-aminoalkoxyborane complex of the formula (I):

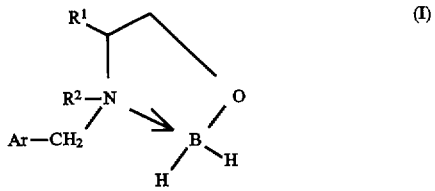

wherein $R^1$ is $C_1$–$C_8$ alkyl, $C_3$–$C_7$ cycloalkyl, $C_7$–$C_{11}$ aralkyl or $C_6$–$C_{10}$ aryl, $R^2$ is hydrogen, $C_1$–$C_8$ alkyl, $C_3$–$C_7$ cycloalkyl or $C_7$–$C_{11}$ aralkyl, or $R^1$ and $R^2$ together form $(CH_2)_n$ wherein n is 3 or 4, and Ar is naphthyl, anthryl or phenanthryl, which may be substituted by from 1 to 3 substituents selected from the group consisting of halogen, nitro, $C_1$–$C_6$ alkyl, $C_3$–$C_7$ cycloalkyl, $C_2$–$C_6$ alkenyl, $C_2$–$C_6$ alkynyl, $C_7$–$C_{11}$ aralkyl, $C_6$–$C_{10}$ aryl, $C_1$–$C_6$ alkoxy and styrene polymer substituents.

The present invention also provides an optically active β-aminoalcohol compound of the formula (II):

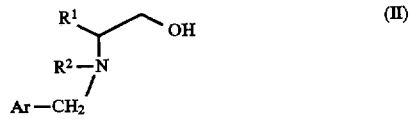

wherein $R^1$ is $C_1$–$C_8$ alkyl, $C_3$–$C_7$ cycloalkyl, $C_7$–$C_{11}$ aralkyl or $C_6$–$C_{10}$ aryl, $R^2$ is hydrogen, $C_1$–$C_8$ alkyl or $C_7$–$C_{11}$ aralkyl, or $R^1$ and $R^2$ together form $(CH_2)_n$ wherein n is 3 or 4, and Ar is naphthyl, anthryl or phenanthryl, which may be substituted by from 1 to 3 substituents selected from the group consisting of halogen, nitro, $C_1$–$C_6$ alkyl, $C_3$–$C_7$ cycloalkyl, $C_2$–$C_6$ alkenyl, $C_2$–$C_6$ alkynyl, $C_7$–$C_{11}$ aralkyl, $C_6$–$C_{10}$ aryl, $C_1$–$C_6$ alkoxy and styrene polymer substituents.

Further, the present invention provides a process for producing an optically active alcohol compound of the formula (IV):

wherein $R^3$ and $R^4$ differ from each other and represent $C_1$–$C_{10}$ alkyl, $C_3$–$C_{10}$ cycloalkyl, $C_2$–$C_{10}$ alkenyl, $C_2$–$C_{10}$ alkynyl, $C_3$–$C_{10}$ cycloalkenyl, $C_7$–$C_{11}$ aralkyl, and $C_6$–$C_{14}$ aryl, or $R^3$ and $R^4$ together form a cyclic structure, and * indicates an optically active center, which comprises reducing a carbonyl compound of the formula (III):

wherein $R^3$ and $R^4$ are as defined above, with the optically active β-aminoalkoxyborane complex as defined above.

Furthermore, the present invention provides a process for producing a compound of the formula (VI).

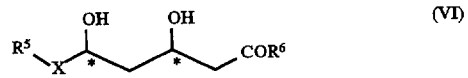

wherein when X is a bond, $R^5$ is CHO, $CH(OR^9)(OR^{10})$ (wherein each of $R^9$ and $R^{10}$ which are independent of each other, is hydrogen or $C_1$–$C_3$ alkyl, or $R^9$ and $R^{10}$ together form $C_2$–$C_5$ alkylene), $CH_2OR^{11}$ (wherein $R^{11}$ is hydrogen, $C_1$–$C_3$ alkyl, benzyl which may be substituted by methyl or methoxy, trityl, tetrahydropyranyl, methoxymethyl, trimethylsilyl, dimethyl-tert-butylsilyl or diphenyl-tert-butylsilyl), $CH_2R^{12}$ (wherein $R^{12}$ is fluoro, chloro, bromo or iodo), CN, $CO_2R^{13}$ (wherein $R^{13}$ is hydrogen, $C_1$–$C_4$ alkyl, or benzyl which may be substituted by methyl or methoxy), or $CONR^{14}R^{15}$ (wherein each of $R^{14}$ and $R^{15}$ which are independent of each other, is hydrogen, $C_1$–$C_3$ alkyl, benzyl, 1-methylbenzyl, or phenyl which may be substituted by methyl or methoxy), and when X is —$CH_2$—, —$CH_2CH_2$—, —CH=CH—, —$(CH_3)C$=CH—, —CH=$C(CH_3)$— or —C≡C—, $R^5$ is hydrogen, trialkylsilyl, a carbon ring aliphatic group, a carbon ring aromatic group, a heterocyclic aromatic group, a condensed heterocyclic aromatic group, a chain unsaturated aliphatic group or a cyclic unsaturated aliphatic group, and $R^6$ is hydroxyl, $C_1$–$C_{10}$ alkoxy, OM (wherein M is lithium, sodium, potassium, calcium, $NHR'_3$ (wherein R' is hydrogen, $C_1$–$C_3$ alkyl, $C_3$–$C_7$ cycloalkyl, $C_2$–$C_5$ alkenyl, phenyl or benzyl)) or $C_0$–$C_7$ amino, and * is an optically active center, provided that the two optically active centers take a syn conformation to each other, which comprises reducing a carbonyl compound of the formula (V):

wherein $R^5$, $R^6$ and X are as defined above, and each of Y and Z which are independent of each other, is —CO— or —CH(OH)—, provided that Y and Z are not simultaneously —CH(OH)—, with the optically active β-aminoalkoxyborane complex as defined above.

Still further, the present invention provides a process for producing a compound of the formula (VI-1):

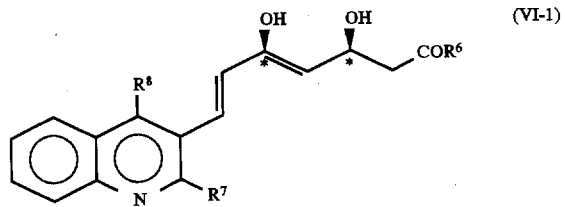

wherein $R^6$ is hydroxyl, $C_1$–$C_{10}$ alkoxy, OM (wherein M is lithium, sodium, potassium, calcium, $NHR'_3$ (wherein R' is hydrogen, $C_1$–$C_3$ alkyl, $C_3$–$C_7$ cycloalkyl, $C_2$–$C_5$ alkenyl, phenyl or benzyl)) or $C_0$–$C_7$ amino, $R^7$ is $C_1$–$C_7$ alkyl or $C_3$–$C_7$ cycloalkyl, $R^8$ is phenyl which may be substituted by $C_1$–$C_7$ alkyl, fluoro, chloro or bromo, * indicates an optically active center, provided that the two optically active centers take a syn conformation to each other, which comprises reducing a 1,3-dicarbonyl compound of the formula (V-1):

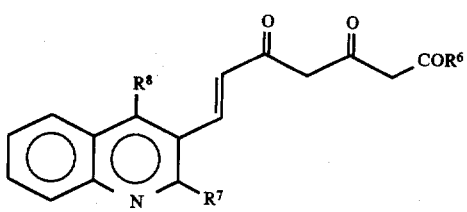

wherein $R^6$, $R^7$ and $R^8$ are as defined above, with the optically active β-aminoalkoxyborane complex as defined above.

Furthermore, the present invention provides a process for producing an optically active 1,3-syn-diol compound of the formula (VI-2):

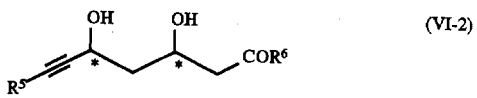

wherein $R^5$ is hydrogen, trialkylsilyl, a carbon ring aliphatic group, a carbon ring aromatic group, a heterocyclic aromatic group, a condensed heterocyclic aromatic group, a chain unsaturated aliphatic group or a cyclic unsaturated aliphatic group, $R^6$ is hydroxyl, $C_1$–$C_{10}$ alkoxy, OM (wherein M is lithium, sodium, potassium, calcium, $NHR'_3$ (wherein R' is hydrogen, $C_1$–$C_3$ alkyl, $C_3$–$C_7$ cycloalkyl, $C_2$–$C_5$ alkenyl, phenyl or benzyl)) or $C_0$–$C_7$ amino, and * indicates an optically active center, provided that the two optically active centers take a syn conformation to each other, which comprises reducing a 1,3-dicarbonyl compound of the formula (V-2):

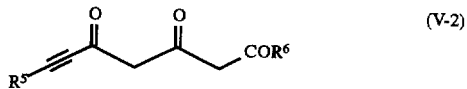

wherein $R^5$ and $R^6$ are as defined above, with the optically active β-aminoalkoxyborane complex as defined above.

In this specification, n represents normal, i iso, sec secondary, tert tertiary, Me methyl, Et ethyl, Bu butyl, Ph phenyl, and THF tetrahydrofuran.

BEST MODE FOR CARRYING OUT THE INVENTION

Now, the compounds of the present invention will be described in detail. The following substituents may be mentioned as substituents for $R^1$ of each of the formulas (I) and (II).

$C_1$–$C_8$ alkyl includes, for example, methyl, ethyl, n-propyl, i-propyl, n-buryl, i-butyl, sec-butyl, tert-butyl, n-pentyl, n-hexyl, n-heptyl and n-octyl.

$C_3$–$C_7$ cycloalkyl includes, for example, cyclopropyl, cyclobutyl, cyclopentyl, cyclohexyl and cycloheptyl.

$C_7$–$C_{11}$ aralkyl includes, for example, benzyl, o-methmethylbenzyl, m-methylbenzyl, p-methylbenzyl, p-chlorobenzyl, 1-methylbenzyl, phenethyl, o-methylphenethyl, m-methylphenethyl, p-methylphenethyl, 3-phenylpropyl, 3-(o-methylphenyl)propyl, 3-(m-methylphenyl)propyl, 3-(p-methylphenyl)propyl, 4-phenylbutyl, α-naphthylmethyl and β-naphthylmethyl.

$C_6$–$C_{10}$ aryl includes, for example, phenyl, o-tolyl, m-tolyl, p-tolyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 3,4,5-trimethylphenyl, 3,4,6-trimethylphenyl, 2,4,6-trimethylphenyl, α-naphthyl and β-naphthyl.

$C_1$–$C_8$ alkyl, $C_3$–$C_7$ cycloalkyl and $C_7$–$C_{11}$ aralkyl as substituents for $R^2$ are the same as the corresponding substituents for $R^1$.

Ar is naphthyl, anthryl or phenanthryl, which may optionally be substituted by from 1 to 3 substituents selected from the group consisting of halogen, nitro, $C_1$–$C_6$ alkyl, $C_3$–$C_7$ cycloalkyl, $C_2$–$C_6$ alkenyl, $C_2$–$C_6$ alkynyl, $C_7$–$C_{11}$ aralkyl, $C_6$–$C_{10}$ aryl, $C_1$–$C_6$ alkoxy and styrene polymer substituents. The respective substituents will be described below.

Halogen includes fluorine, chlorine, bromine and iodine.

$C_1$–$C_6$ alkyl includes, for example, methyl, ethyl, n-propyl, i-propyl, n-butyl, i-butyl, sec-butyl, tert-butyl, n-pentyl and n-hexyl.

$C_3$–$C_7$ cycloalkyl is the same as the corresponding substituent for $R^1$.

$C_2$–$C_6$ alkenyl includes, for example, vinyl, 2-propenyl, 3-butenyl, 4-pentenyl and 5-hexenyl.

$C_2$–$C_6$ alkynyl includes, for example, ethynyl, 2-propynyl, 3-butynyl, 4-pentynyl and 5-hexynyl.

$C_1$–$C_6$ alkoxy includes, for example, methoxy, ethoxy, n-propoxy, i-propoxy, n-butoxy, i-butoxy, sec-butoxy, tert-butoxy, n-pentoxy and n-hexoxy.

The compounds of the formulas (I) and (II) of the present invention include, for example, compounds presented in Table 1. However, it should be understood that the compounds of the present invention are not restricted to such specific examples. Here, Me represents a methyl group, t-Bu a tetiary buryl group, and Ph a phenyl group.

TABLE 1
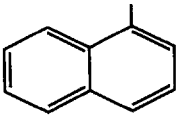
| $R^1$ | $R^2$ | Ar |
|---|---|---|
| CH$_3$ | CH$_3$ | 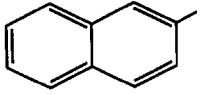 |
| CH$_3$ | t-Bu | 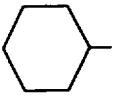 |
| CH$_3$ | 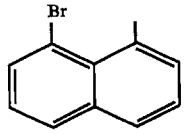 | 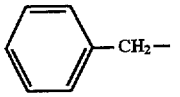 |
| CH$_3$ | 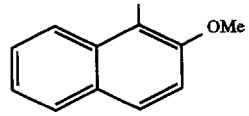 | 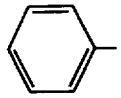 |
| CH$_3$ | 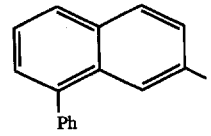 | 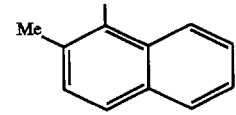 |
| CH$_3$ | CH$_3$ | 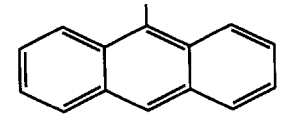 |
| CH$_3$ | t-Bu | 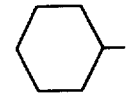 |
| CH$_3$ | 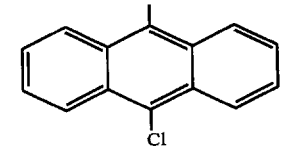 | 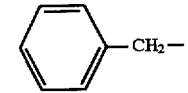 |
| CH$_3$ | 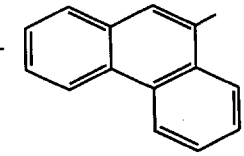 | |

TABLE 1-continued
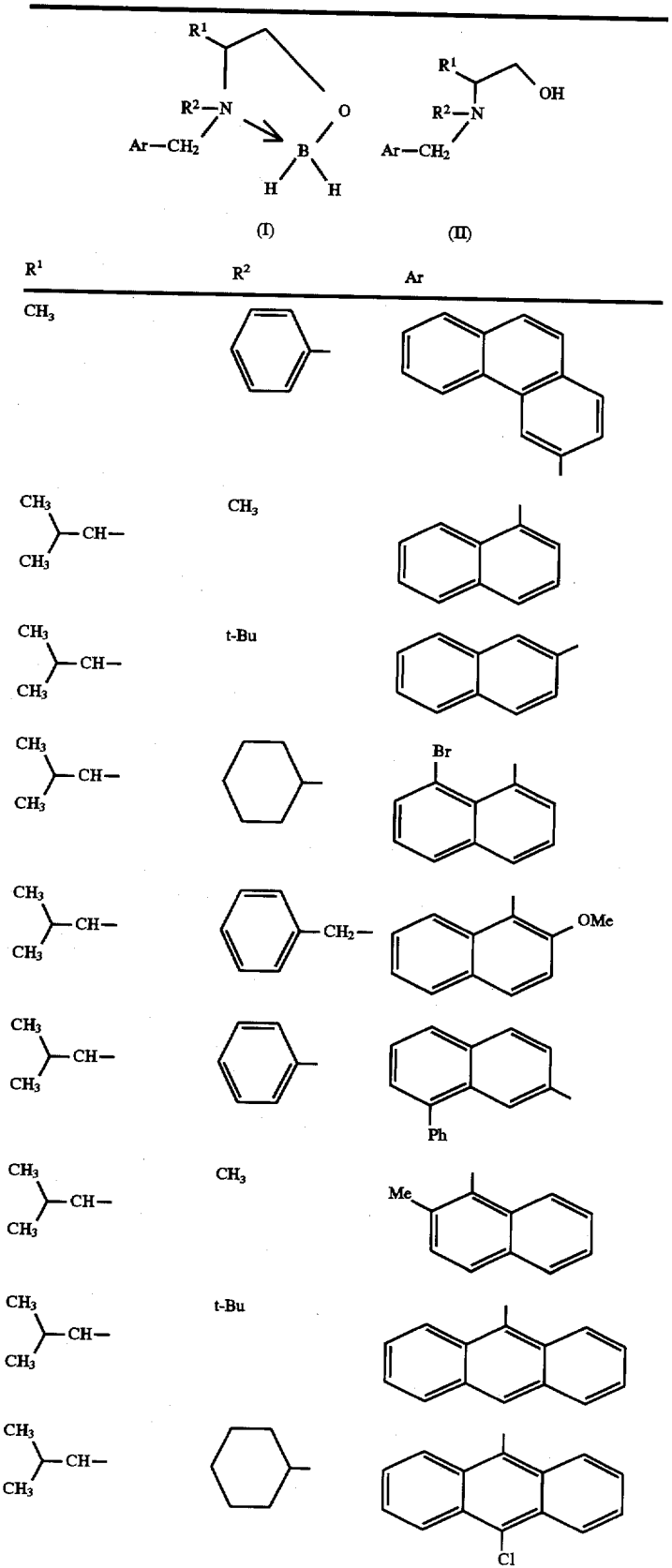

TABLE 1-continued
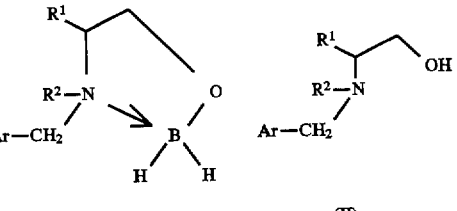
(I)
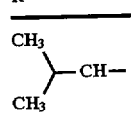
(II)
| R¹ | R² | Ar |
|---|---|---|
| 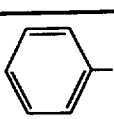 | 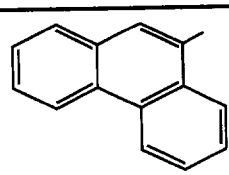 | 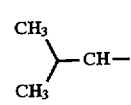 |
| 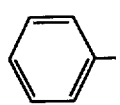 | 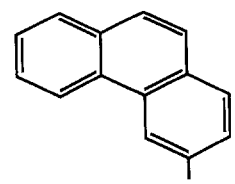 | 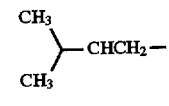 |
| 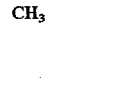 | CH₃ | 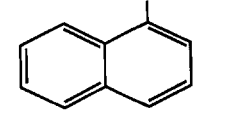 |
| 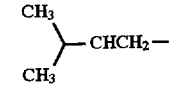 | t-Bu | 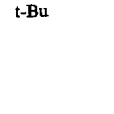 |
| 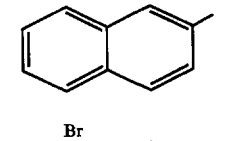 | 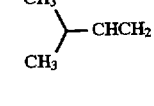 | 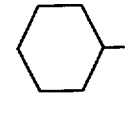 |
| 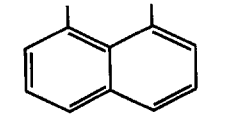 | 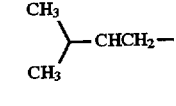 | 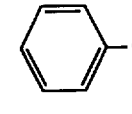 |
| 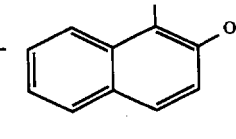 | 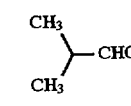 | 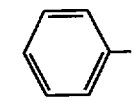 |
| 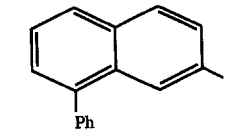 | CH₃ | 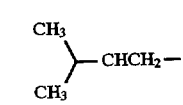 |
| 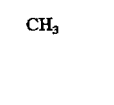 | t-Bu | 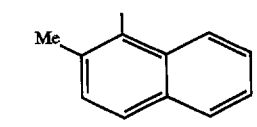 |

TABLE 1-continued

|  | R¹ | | | R¹ | |
|--|--|--|--|--|--|
|  | \ | | | \ | |
|  | R²—N | | | R²—N | OH |
|  | / ↘ O | | | / | |
|  | Ar—CH₂ B / \ | | | Ar—CH₂ | |
|  | H H | | | | |
|  | (I) | | | (II) | |

| R¹ | R² | Ar |
|---|---|---|
| (CH₃)₂CHCH₂— | cyclohexyl | 10-chloroanthracen-9-yl |
| (CH₃)₂CHCH₂— | PhCH₂— | phenanthren-9-yl |
| (CH₃)₂CHCH₂— | phenyl | phenanthren-3-yl |
| CH₃CH₂—CH(CH₃)CH₂— | CH₃ | naphthalen-1-yl |
| CH₃CH₂—CH(CH₃)CH₂— | t-Bu | naphthalen-2-yl |
| CH₃CH₂—CH(CH₃)CH₂— | cyclohexyl | 8-bromonaphthalen-1-yl |
| CH₃CH₂—CH(CH₃)CH₂— | PhCH₂— | 2-methoxynaphthalen-1-yl |
| CH₃CH₂—CH(CH₃)CH₂— | phenyl | 5-phenylnaphthalen-2-yl |
| CH₃CH₂—CH(CH₃)CH₂— | CH₃ | 2-methylnaphthalen-1-yl |

TABLE 1-continued

Structure (I): R¹, R²N(CH₂Ar) coordinated to BH₂-O (cyclic aminoborane)
Structure (II): R¹, R²N(CH₂Ar)-CH(R¹)-CH₂OH (amino alcohol)

| R¹ | R² | Ar |
|---|---|---|
| CH₃CH₂—CH(CH₃)CH₂— | t-Bu | 9-anthracenyl |
| CH₃CH₂—CH(CH₃)CH₂— | cyclohexyl | 10-chloro-9-anthracenyl |
| CH₃CH₂—CH(CH₃)CH₂— | benzyl (PhCH₂—) | phenanthrenyl |
| CH₃CH₂—CH(CH₃)CH₂— | phenyl | phenanthrenyl |
| benzyl (PhCH₂—) | CH₃ | 1-naphthyl |
| benzyl (PhCH₂—) | t-Bu | 2-naphthyl |
| benzyl (PhCH₂—) | cyclohexyl | 8-bromo-1-naphthyl |
| benzyl (PhCH₂—) | benzyl (PhCH₂—) | 2-methoxy-1-naphthyl |
| benzyl (PhCH₂—) | phenyl | 4-phenyl-2-naphthyl |

TABLE 1-continued

Structure (I): amino alcohol-borane complex with substituents $R^1$, $R^2$, Ar—CH$_2$ on N, coordinated to BH$_2$–O.

Structure (II): corresponding amino alcohol with $R^1$, $R^2$, Ar—CH$_2$ on N, and CH$_2$OH group.

| $R^1$ | $R^2$ | Ar |
|---|---|---|
| PhCH$_2$— | CH$_3$ | 1-Me-2-naphthyl |
| PhCH$_2$— | t-Bu | 9-methyl-anthracenyl |
| PhCH$_2$— | cyclohexyl | 10-methyl-9-chloro-anthracenyl |
| PhCH$_2$— | PhCH$_2$— | methyl-phenanthrenyl |
| PhCH$_2$— | phenyl | dimethyl-phenanthrenyl |
| (indol-3-yl)CH$_2$— | CH$_3$ | 1-methyl-naphthyl |
| (indol-3-yl)CH$_2$— | t-Bu | 2-methyl-naphthyl |
| (indol-3-yl)CH$_2$— | cyclohexyl | 1-methyl-8-bromo-naphthyl |

TABLE 1-continued
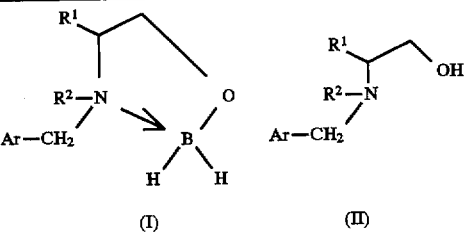
| R¹ | R² | Ar |
|---|---|---|
| 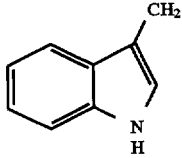 | 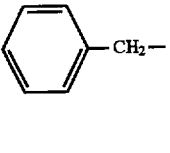 | 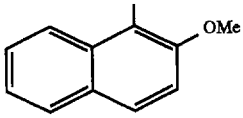 |
|  | 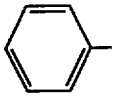 | 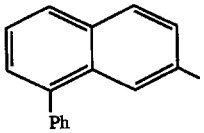 |
| 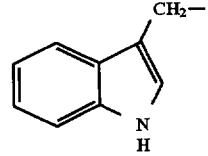 | CH₃ | 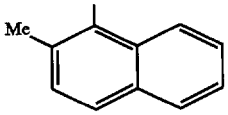 |
|  | t-Bu | 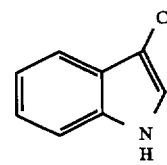 |
| 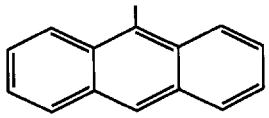 | 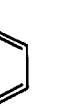 | 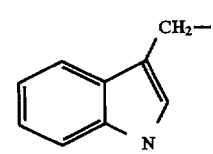 |
| 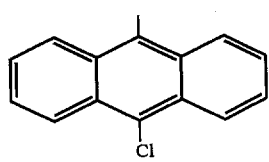 | 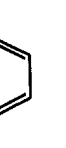 | 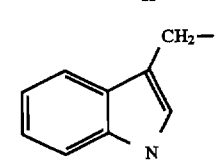 |
| 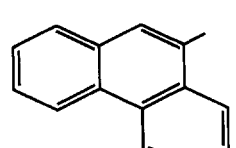 |  | 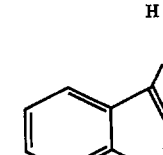 |
| CH₃S—CH₂CH₂— | CH₃ | 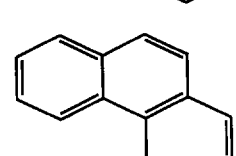 |

TABLE 1-continued
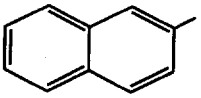
| $R^1$ | $R^2$ | Ar |
|---|---|---|
| $CH_3S-CH_2CH_2-$ | t-Bu | 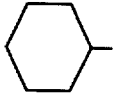 |
| $CH_3S-CH_2CH_2-$ | 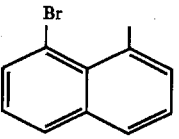 | 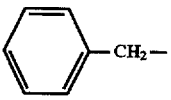 |
| $CH_3S-CH_2CH_2-$ | 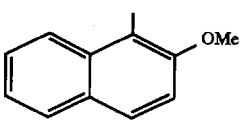—$CH_2-$ | 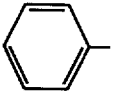 |
| $CH_3S-CH_2CH_2-$ | 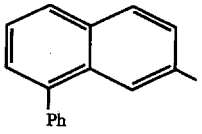 | 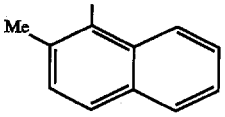 |
| $CH_3S-CH_2CH_2-$ | $CH_3$ | 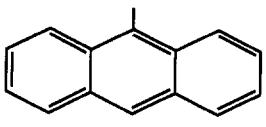 |
| $CH_3S-CH_2CH_2-$ | t-Bu | 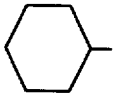 |
| $CH_3S-CH_2CH_2-$ | 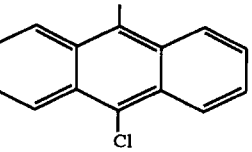 | 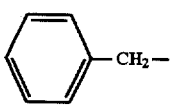 |
| $CH_3S-CH_2CH_2-$ | 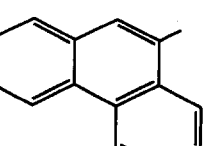—$CH_2-$ |  |
| $CH_3S-CH_2CH_2-$ | 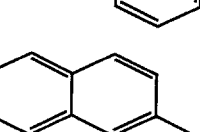 | |

TABLE 1-continued
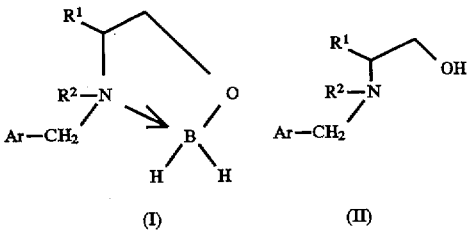
| R¹ | R² | Ar |
|---|---|---|
| HO—CH₂— | CH₃ | 1-naphthyl |
| HO—CH₂— | t-Bu | 2-naphthyl |
| HO—CH₂— | cyclohexyl | 8-bromo-1-naphthyl |
| HO—CH₂— | benzyl | 2-methoxy-1-naphthyl |
| HO—CH₂— | phenyl | 7-phenyl-2-naphthyl (with Ph substituent) |
| HO—CH₂— | CH₃ | 2-methyl-1-naphthyl |
| HO—CH₂— | t-Bu | 10-anthryl |
| HO—CH₂— | cyclohexyl | 10-chloro-9-anthryl |
| HO—CH₂— | benzyl | phenanthryl |

TABLE 1-continued

| R¹ | R² | Ar |
|---|---|---|
| HO—CH₂— | phenyl | phenanthrenyl |
| CH₃—CH(OH)— | CH₃ | 1-naphthyl |
| CH₃—CH(OH)— | t-Bu | 2-naphthyl |
| CH₃—CH(OH)— | cyclohexyl | 8-bromo-1-naphthyl |
| CH₃—CH(OH)— | PhCH₂— | 1-methyl-2-methoxynaphthyl |
| CH₃—CH(OH)— | phenyl | 1-phenyl-7-naphthyl |
| CH₃—CH(OH)— | CH₃ | 1,2-dimethylnaphthyl |
| CH₃—CH(OH)— | t-Bu | 10-methylanthracenyl |
| CH₃—CH(OH)— | cyclohexyl | 10-methyl-Cl-anthracenyl |

TABLE 1-continued $$\underset{(I)}{\overset{R^1}{\underset{Ar-CH_2}{R^2-N}}\overset{O}{\underset{H}{\overset{B}{\diagdown}}H}} \quad \underset{(II)}{\overset{R^1}{\underset{Ar-CH_2}{R^2-N}}\diagdown OH}$$

| $R^1$ | $R^2$ | Ar |
|---|---|---|
| $CH_3-CH(OH)-$ | benzyl ($C_6H_5-CH_2-$) | phenanthren-9-yl |
| $CH_3-CH(OH)-$ | phenyl | phenanthren-3-yl |
| $HS-CH_2-$ | $CH_3$ | naphthalen-1-yl |
| $HS-CH_2-$ | t-Bu | naphthalen-2-yl |
| $HS-CH_2-$ | cyclohexyl | 8-bromonaphthalen-1-yl |
| $HS-CH_2-$ | benzyl | 2-methoxynaphthalen-1-yl |
| $HS-CH_2-$ | phenyl | 8-phenylnaphthalen-2-yl |
| $HS-CH_2-$ | $CH_3$ | 2-methylnaphthalen-1-yl |
| $HS-CH_2-$ | t-Bu | anthracen-9-yl |

TABLE 1-continued

Structures (I) and (II) with substituents R¹, R², Ar as depicted.

| R¹ | R² | Ar |
|---|---|---|
| HS—CH₂— | cyclohexyl | 10-chloroanthracen-9-yl |
| HS—CH₂— | PhCH₂— | phenanthren-9-yl |
| HS—CH₂— | phenyl | phenanthren-2-yl |
| 4-HO-C₆H₄-CH₂— (CH₃) | | naphth-1-yl |
| 4-HO-C₆H₄-CH₂— (t-Bu) | | naphth-2-yl |
| 4-HO-C₆H₄-CH₂— | cyclohexyl-CH₂— | 8-bromonaphth-1-yl |
| 4-HO-C₆H₄-CH₂—C₆H₄-CH₂— | | 2-methoxy-naphth-1-yl |
| 4-HO-C₆H₄-CH₂—C₆H₄— | | 5-phenylnaphth-2-yl |
| 4-HO-C₆H₄-CH₂— (CH₃) | | 2-methylnaphth-1-yl |

TABLE 1-continued

Structure (I): R¹-CH(NR²(CH₂Ar))-CH₂-O→BH₂ 
Structure (II): R¹-CH(NR²(CH₂Ar))-CH₂-OH

| R¹ | R² | Ar |
|---|---|---|
| 4-HO-C₆H₄-CH₂- | t-Bu | 9-anthracenyl |
| 4-HO-C₆H₄-CH₂- | cyclohexyl | 10-chloro-9-anthracenyl |
| 4-HO-C₆H₄-CH₂- | C₆H₅-CH₂- | 2-phenanthrenyl |
| 4-HO-C₆H₄-CH₂- | C₆H₅- | 3-phenanthrenyl |
| (4-imidazolyl)-CH₂- | CH₃ | 1-naphthyl |
| (4-imidazolyl)-CH₂- | t-Bu | 2-naphthyl |
| (4-imidazolyl)-CH₂- | cyclohexyl | 8-bromo-1-naphthyl |
| (4-imidazolyl)-CH₂- | C₆H₅-CH₂- | 3-methoxy-1-naphthyl |
| (4-imidazolyl)-CH₂- | C₆H₅- | 8-phenyl-2-naphthyl |

TABLE 1-continued
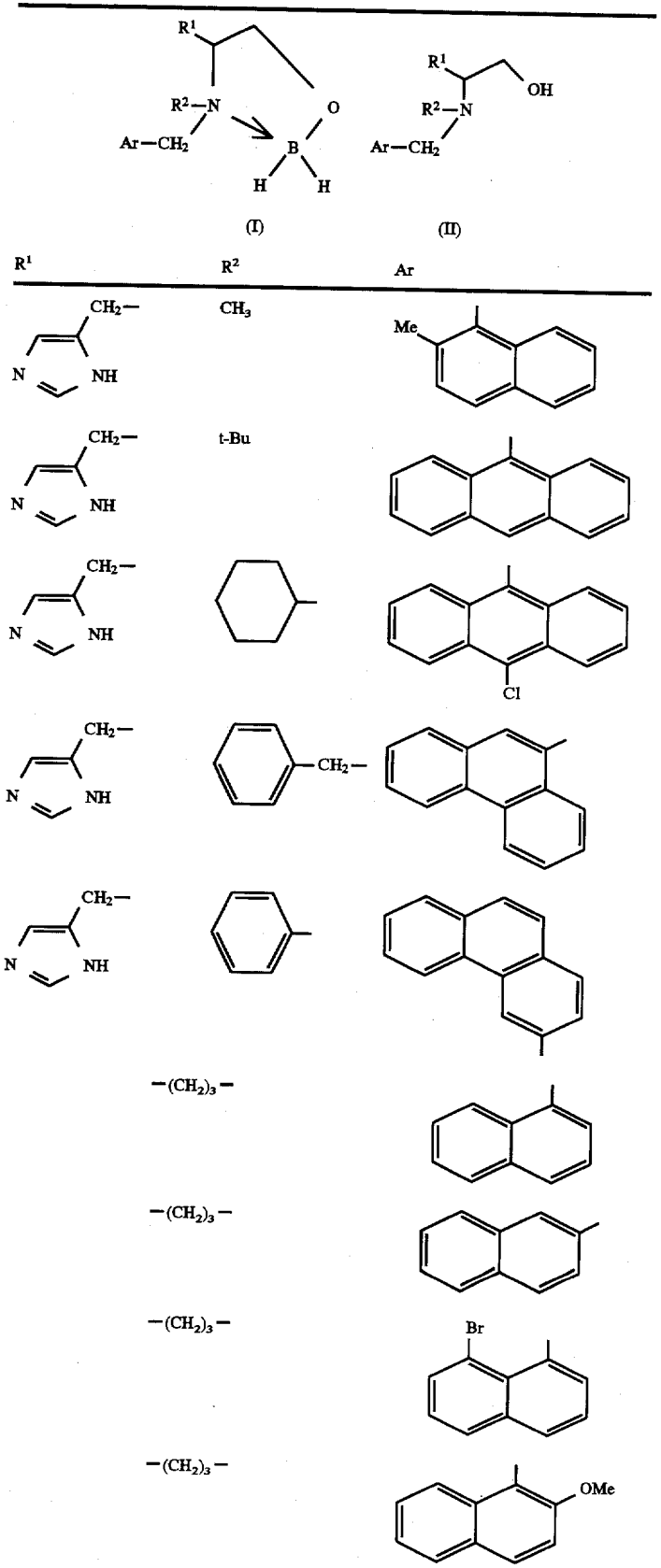

TABLE 1-continued
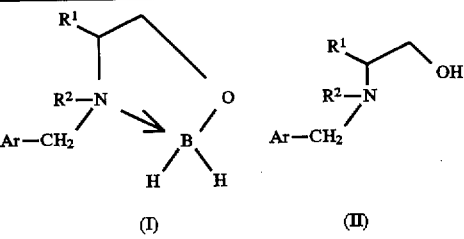
| R¹ | R² | Ar |
|---|---|---|
| | —(CH$_2$)$_3$— | 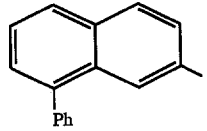 |
| | —(CH$_2$)$_3$— | 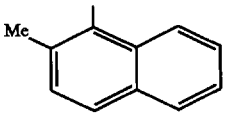 |
| | —(CH$_2$)$_3$— | 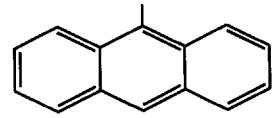 |
| | —(CH$_2$)$_3$— | 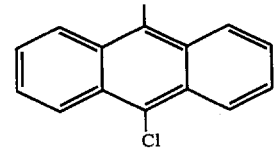 |
| | —(CH$_2$)$_3$— | 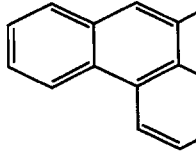 |
| | —(CH$_2$)$_3$— | 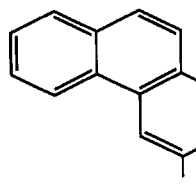 |
| | —(CH$_2$)$_4$— | 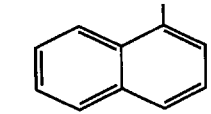 |
| | —(CH$_2$)$_4$— | 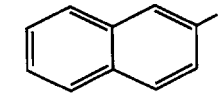 |
| | —(CH$_2$)$_4$— | 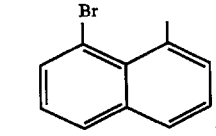 |

TABLE 1-continued

| | | |
|---|---|---|
| (I) | (II) | |

| $R^1$ | $R^2$ | Ar |
|---|---|---|
| $-(CH_2)_4-$ | | naphthyl-OMe |
| $-(CH_2)_4-$ | | naphthyl-Ph |
| $-(CH_2)_4-$ | | naphthyl-Me |
| $-(CH_2)_4-$ | | anthracenyl |
| $-(CH_2)_4-$ | | chloroanthracenyl |
| $-(CH_2)_4-$ | | phenanthrenyl |
| $-(CH_2)_4-$ | | phenanthrenyl |

Now, the synthesis of the borane complex (I) and the asymmetric reaction of a carbonyl compound using the borane complex will be described in detail.

The optically active β-aminoalcohol compound (II) and its borane complex (I) according to the present invention, can readily be produced in good yield in two or three steps using, as starting material, an optically active β-aminoalcohol (VIII) which is again readily available from an amino acid ester, by known methods (JIKKEN KAGAKU KOZA 17, YUKI KAGOBUTSU NO HANNO (GE) p. 25, P. Karrer, P. Portmann and M. Surer, Helv. Chim. Acta, 31, 1617 (1948); P. Karrer and P. Portmann, ibid., 32, 1034 (1949); P. Karrer, P. Portmann and M. Suter, ibid., 32, 1156 (1949); R. R. Gebhard and P. Karrer, ibid., 38, 915 (1955); Synthetic Methods of Organic Chemistry Vol. 11, 52; H. Bauer, E. Adams and H. Tabor, Biochem. Prep. 4, 46 (1955)).

The following reaction scheme represents a synthetic route of the optically active β-aminoalkoxyborane complex of the formula (I) and the optically active β-aminoalcohol compound of the formula (II). In the formulas, $R^1$, $R^2$ and Ar are as defined above.

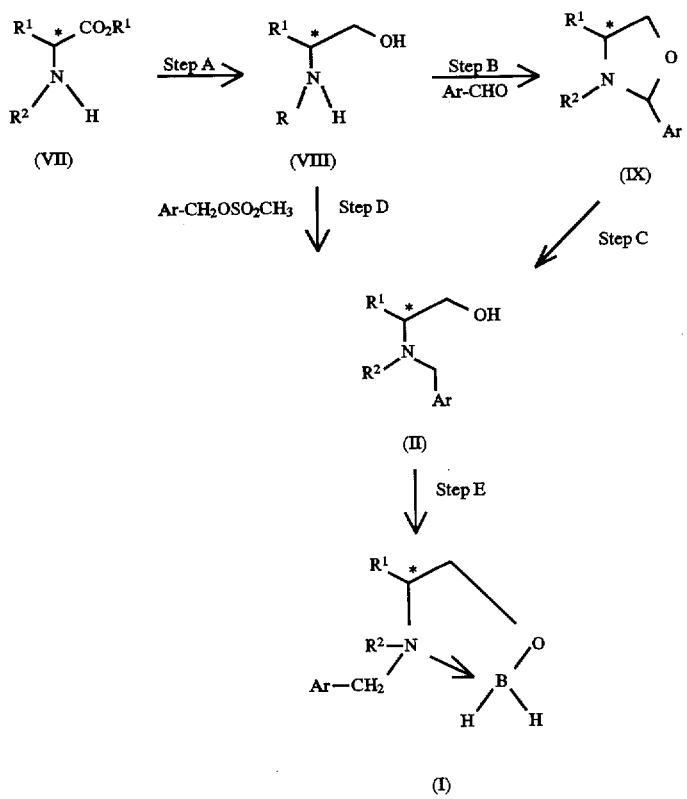

Step A is a reduction reaction of the ester moiety of the amino acid ester (VII) to an alcohol (VIII). As the reducing agent, lithium aluminum hydride, diisobutylaluminum hydride, sodium dialkoxyaluminum hydride or lithium borohydride may, for example, be used. Preferably, lithium aluminum hydride is employed. As the solvent for reaction, an ether type solvent such as diethyl ether, di-n-propyl ether, tetrahydrofuran, 1,3- or 1,4-dioxane may be employed. Preferably, diethyl ether or tetrahydrofuran is employed. The reaction can be conducted within a temperature range of from −78° C. to 60° C., preferably from −10° C. to 20° C.

Step B is a reaction for forming an oxazolidine ring by a dehydration condensation reaction of the β-aminoalcohol (VIII) obtained in Step A with the aromatic aldehyde. The solvent for reaction may, for example, be an alcohol solvent such as methanol, ethanol, n-propanol or i-propanol, a polar solvent such as acetonitrile, dimethylformamide or dimethylsulfoxide, a halogen-type solvent such as dichloromethane, 1,1- or 1,2-dichloroethane, chloroform or carbon tetrachloride, or an ether type solvent such as diethyl ether, di-n-propyl ether, tetrahydrofuran, 1,3- or 1,4-dioxane. Preferably, methanol, acetonitrile or tetrahydrofuran is employed. The reaction can be conducted within a temperature range of from −78° C. to 60° C., preferably from −10° C. to 30° C.

Step C is a reaction to obtain an N-(aryl)methyl-β-aminoalcohol compound (II) by reductive ring-opening of the oxazolidine compound (IX) obtained in step B. As the reducing agent, lithium aluminum hydride, diisobutyl aluminum hydride, sodium dialkoxyaluminum hydride, lithium borohydride, potassium borohydride or sodium borohydride may, for example, be employed. Preferably, potassium borohydride or sodium borohydride is employed. The solvent for reaction may, for example, be an alcohol-type solvent such as methanol, ethanol, n-propanol or i-propanol, or an ether-type solvent such as diethyl ether, di-n-propyl ether, tetrahydrofuran, 1,3- or 1,4-dioxane. Preferably, methanol, ethanol or tetrahydrofuran is employed. The reaction can be conducted within a temperature range of from −78° C. to 60 C., preferably from −10° C. to 20° C.

Step D is another synthetic route for the N-(aryl)methyl-β-aminoalcohol compound (II). Namely, the N-(aryl)methyl-β-aminoalcohol compound (II) is obtained by the reaction of the β-aminoalcohol compound (VIII) with the corresponding arylmethyl ester of sulfonic acid.

As the sulfonate having an arylmethyl group, methylate, benzene sulfonate, p-chlorobenzene sulfonate, p-toluene sulfonate, p-nitrobenzene sulfonate or trifluoromethane sulfonate may, for example, be employed. Preferably methylate is employed. As the base, a tertiary or unsaturated amine such as triethylamine, trimethylamine, pyridine, DBU (1,8-diazabicyclo[5.4.0]-7-undecene) or DBN (1,5-diazabicyclo[4.3.0]-5-nonene) may be employed. Preferably triethylamine is employed. The solvent for reaction may, for example, be an ether-type solvent such as diethyl ether, di-n-propyl ether, tetrahydrofuran, 1,3- or 1,4-dioxane, a polar solvent such as acetonitirile, dimethylformamide or dimethylsulfoxide, or a halogen-type solvent such as dichloromethane, 1,1- or 1,2-dichloroethane, chloroform, or carbon tetrachloride. Preferably dichloromethane or chloroform is employed, more preferably dichloromethane is employed. The reaction can be conducted within a temperature range of from −78° C. to 60° C., preferably from −10° C. to 30° C.

Step E is a reaction for synthesizing the β-aminoalkoxyborane complex (I) by the reaction of the N-(aryl)methyl-β-aminoalcohol compound (II) obtained in Step C or D with a borane reagent. As the borane reagent, a borane-tetrahydrofuran complex, a borane-diethyl ether complex, a borane-pyridine complex, a borane.ammonia complex, a borane.tert-butylamine complex, a borane.N,N-diethylaniline complex, a borane.N,N-diisopropylethylamine complex, a borane.dimethylamine complex, a borane.4-dimethylaminopyridine complex, a borane.4-ethylmorpholine complex, a borane.methylsulfide complex, a borane.trimethylamine complex, a borane.triphenylphosphine complex or a borane.triphenylphosphite complex, may, for example, be used. Preferably, a borane-.tetrahydrofuran complex or a borane.diethyl ether complex is used. More preferably, a boranetetrahydrofuran complex is employed. The solvent for reaction may, for example, be an alcohol such as methanol, ethanol, n-propanol or i-propanol, a polar solvent such as acetonitrile, dimethylformamide or dimethylsulfoxide, a halogen-type solvent such as dichloromethane, 1,1- or 1,2-dichloroethane, chloroform or carbon tetrachloride, or an ether-type solvent such as diethyl ether, di-n-propyl ether, tetrahydrofuran, 1,3- or 1,4-dioxane. Preferably, methanol, dichloromethane, diethyl ether or tetrahydrofuran is used. More preferably, tetrahydrofuran is used. The reaction can be conducted within a temperature range of from $-100°$ C. to $80°$, preferably from $-78°$ C. to $40°$ C.

The β-aminoalkoxyborane complex (I) is stable against light, water and heat and soluble in various solvents, and thus has a merit that it is very easy to handle for experiments.

Further, in some cases, the β-aminoalkoxyborane complex (I) may be formed in the reaction system by adding the N-(aryl)methyl-β-aminoalcohol compound (II) and the borane reagent to the reaction system at the time of the reduction reaction of the carbonyl compound, without separating it for use.

The carbonyl compound (III) or (V) is stereoselectively reduced by means of the optically active β-aminoalkoxyborane complex (I) obtained in Step E to obtain the corresponding optically active alcohol compound (IV) or (VI).

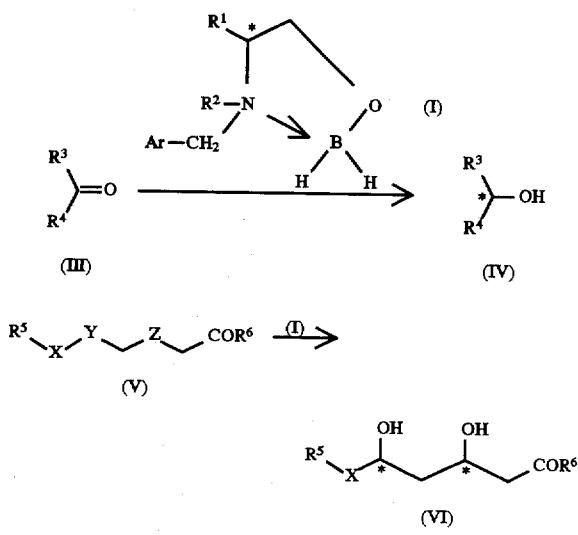

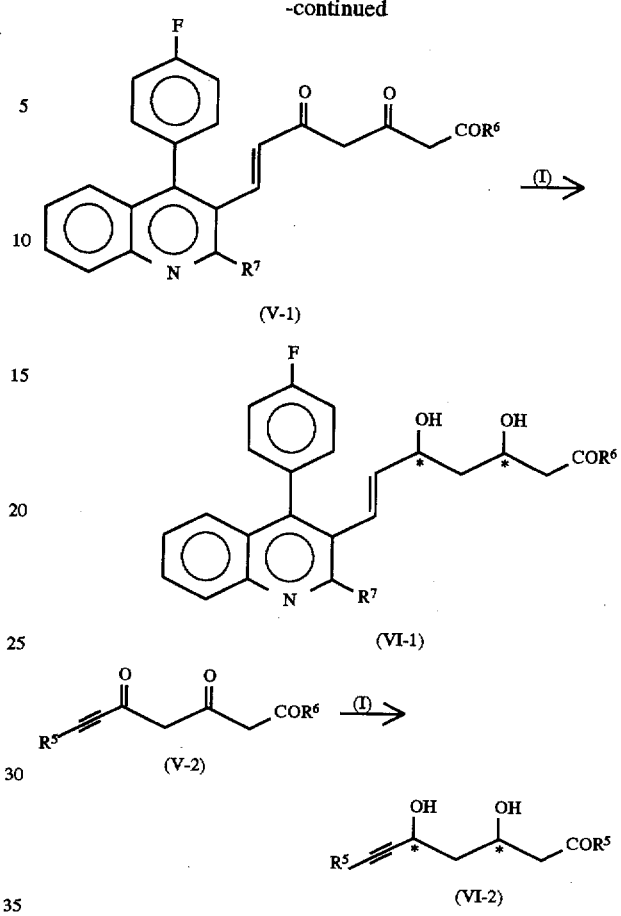

The respective substituents of the compounds of the formulas (III), (IV), (V) and (VI) will now be described.

$R^3$ and $R^4$ differ from each other and represent $C_1$–$C_{10}$ alkyl, $C_3$–$C_{10}$ cycloalkyl, $C_2$–$C_{10}$ alkenyl, $C_2$–$C_{10}$ alkynyl, $C_3$–$C_{10}$ cycloalkenyl, $C_7$–$C_{11}$ aralkyl or $C_6$–$C_{14}$ aryl. Otherwise, $R^3$ and $R^4$ may together form a cyclic structure.

$C_1$–$C_{10}$ alkyl includes, for example, methyl, ethyl, n-propyl, i-propyl, n-butyl, i-butyl, sec-butyl, tert-butyl, n-pentyl, n-hexyl, n-heptyl, n-octyl, n-nonyl and n-decanyl.

$C_3$–$C_{10}$ cycloalkyl includes, for example, cyclopropyl, cyclobutyl, cyclopentyl, cyclohexyl, cycloheptyl, cyclooctyl, cyclononyl and cyclodecanyl.

$C_2$–$C_{10}$ alkenyl includes, for example, vinyl, 1-propenyl, 1-methylethenyl, 2-propenyl, 1,2-dimethyl-1-propenyl, 1-butenyl, 1-pentenyl, 1-hexenyl, 1-heptenyl, 1-octenyl, 1-nonenyl and 1-decenyl.

$C_2$–$C_{10}$ alkynyl includes, for example, ethynyl, 1-propynyl, 2-propynyl, 1-butynyl, 3-methyl-1-butynyl, 1-pentynyl, 1-hexynyl, 1-heptynyl, 1-octynyl, 1-nonynyl and 1-decynyl.

$C_3$–$C_{10}$ cycloalkenyl includes, for example, 2-cyclopropenyl, 1-cyclobutenyl, 3-cyclopentenyl, 1-cyclohexenyl, 2-cyclohexenyl and 3-cyclohexenyl.

$C_7$–$C_{11}$ aralkyl is the same as the corresponding substituent for $R^1$.

$C_6$–$C_{14}$ aryl includes, for example, phenyl, o-tolyl, m-tolyl, p-tolyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 3,4,6-trimethylphenyl, 2,4,6- trimethylphenyl, 2-chlorophenyl, 3-chlorophenyl, 4-chlorophenyl, 3,4-dichlorophenyl, 2-methoxyphenyl, 3-methoxyphenyl, 4-methoxyphenyl, 3,4-dimethoxyphenyl, 3-nitrophenyl, α-naphthyl, β-naphthyl, (2-methyl)-2-naphthyl, (3-methyl)-1-naphthyl, (4-methyl)-1-naphthyl, (5-methyl)-1-naththyl, (6-methyl)-1-naphthyl, (7-methyl)-1-naphthyl, (8-methyl)-1-naphthyl, (1-methyl)-2-naphthyl, (3-methyl)-2-naphthyl, (4-methyl)-2-naphthyl, (5-methyl)-2-naphthyl, (6-methyl)-2-naphthyl, (7-methyl)-2-naphthyl, (8-methyl)-2-naphthyl, (2-ethyl)-1-naphthyl, (3-ethyl)-1-naphthyl, (4-ethyl)-1-naphthyl), (5-ethyl)-1-naphthyl, (6-ethyl)-1-naphthyl, (7-ethyl)-1-naphthyl, (8-ethyl)-1-naphthyl, (1-ethyl)-2-naphthyl, (3-ethyl)-2-naphthyl, (4-ethyl)-2-naphthyl, (5-ethyl)-2-naphthyl, (6-ethyl)-2-naphthyl, (7-ethyl)-2-naphthyl, (8-ethyl)-2-naphthyl, (2-propyl)-1-naphthyl, (3-propyl)-1-naphthyl, (4-propyl)-1-naphthyl, (5-propyl)-1-naphthyl, (6-propyl)-1-naphthyl, (7-propyl)-1-naphthyl, (8-propyl)-1-naphthyl, (1-propyl)-2-naphthyl, (3-propyl)-2-naphthyl, (4-propyl)-2-naphthyl, (5-propyl)-2-naphthyl, (6-propyl)-2-naphthyl, (7-propyl)-2-naphthyl, (8-propyl)-2-naphthyl, 1-anthryl, 2-anthryl, 9-anthryl, 1-phenanthryl, 3-phenanthryl, 4-phenanthryl and 9-phenanthryl.

The cyclic structure formed by $R^3$ and $R^4$ together includes, for example, 1-methylcyclobutanone, 2,2-dimethylcyclobutanone, 2,2-ethylcyclobutanone, 2,2-di-n-cyclobutanone, 2,2-di-i-propylcyclobutanone, 2,2-di-n-butylcyclobutanone, 2,2-di-i-butylcyclobutanone, 2,2-di-sec-butylcyclobutanone, 2,2-di-tert-butylcyclobutanone, 2,2-di-n-pentylcyclobutanone, 2,2-di-n-hexylcyclobutanone, 1-methylcyclopentanone, 2,2-dimethylcyclopentanone, 2,2-diethylcyclopentanone, 2,2-di-n-propylcyclopentanone, 2,2-di-i-propylcyclopentanone, 2,2-di-n-butylcyclopentanone, 2,2-di-i-butylcyclopentanone, 2,2-di-sec-butylcyclopentanone, 2,2-di-tert-butylcyclopentanone, 2,2-di-n-pentylcyclopentanone, 2,2-di-n-hexylcyclopentanone, trimethylcyclohexanone, 2,2-dimethylcyclohexanone, 2,2-diethylcyclohexanone, 2,2-di-n-propylcyclohexanone, 2,2-di-i-propylcyclohexanone, 2,2-di-n-butylcyclohexanone, 2,2-di-i-butylcyclohexanone, 2,2-di-sec-butylcyclohexanone, 2,2-di-tert-butylcyclohexanone, 2,2-di-n-pentylcyclohexanone, 2,2-di-n-hexylcyclohexanone, cyclobutenone, 2-cyclopentenone, 2-cyclohexenone, 2-cycloindanone and 1-tetralone.

X represents a bond, —$CH_2$—, —$CH_2CH_2$—, —CH=CH—, —($CH_3$)C=CH—, —CH=C($CH_3$)— or —C≡C—.

When X is a bond, $R^5$ is CHO, CH(O$R^9$)(O$R^{10}$) (wherein each of $R^9$ and $R^{10}$ which are independent of each other, is hydrogen or $C_1$–$C_3$ alkyl, or $R^9$ and $R^{10}$ together form $C_2$–$C_5$ alkylene), $CH_2OR^{11}$ (wherein $R^{11}$ is hydrogen, $C_1$–$C_3$ alkyl, benzyl which may be substituted by methyl or methoxy, trityl, tetrahydropyranyl, methoxymethyl, trimethylsilyl, dimethyl-tert-butylsilyl or diphenyl-tert-butylsilyl), $CH_2R^{12}$ (wherein $R^{12}$ is fluoro, chloro, bromo or iodo), CN, $CO_2R^{13}$ (wherein $R^{13}$ is hydrogen, $C_1$–$C_4$ alkyl, or benzyl which may be substituted by methyl or methoxy), or $CONR^{14}R^{15}$ (wherein each of $R^{14}$ and $R^{15}$ which are independent of each other, is hydrogen, $C_1$–$C_3$ alkyl group, benzyl, 1-methylbenzyl, or phenyl which may be substituted by methyl or methoxy).

Each of $R^9$ and $R^{10}$ which are independent of each other, may be hydrogen, methyl, ethyl, n-propyl or i-propyl, or $R^9$ and $R^{10}$ may together form ethylene, trimethylene or 2,2-dimethyl-1,3-trimethylene.

$R^{11}$ may be hydrogen, methyl, ethyl, n-propyl, i-propyl, o-methylbenzyl, m-methylbenzyl, p-methylbenzyl, o-methoxybenzyl, m-methoxybenzyl, p-methoxybenzyl, trithyl, tetrahydropyranyl, methoxymethyl, trimethylsilyl, dimethyl-tert-butylsilyl or diphenyl-tert-butylsilyl.

$R^{12}$ is fluoro, chloro, bromo or iodo.

$R^{13}$ may be hydrogen, methyl, ethyl, n-propyl, i-propyl, n-butyl, i-butyl, t-butyl, o-methylbenzyl, m-methylbenzyl, p-methylbenzyl, o-methoxybenzyl, m-methoxybenzyl or p-methoxybenzyl.

Each of $R^{14}$ and $R^{15}$ which are independent of each other, may be hydrogen, methyl, ethyl, n-propyl, i-propyl, benzyl, 1-methylbenzyl, o-methylphenyl, o-methylphenyl, p-methylphenyl, o-methoxyphenyl, m-methoxyphenyl or p-methoxyphenyl.

When X is —$CH_2$—, —$CH_2CH_2$—, —CH=CH—, —($CH_3$)C=CH—, —CH=C($CH_3$)— or —C≡C—, $R^5$ is hydrogen, trialkylsilyl, a carbon ring aliphatic group, a carbon ring aromatic group, a heterocyclic aromatic group, a condensed heterocyclic aromatic group, a chain unsaturated aliphatic group or a cyclic unsaturated aliphatic group. cyclic unsaturated aliphatic group.

Trialkylsilyl includes, for example, trimethylsilyl, triethylsilyl, tri-n-propylsilyl, tri-i-propylsilyl, tri-n-butylsilyl, tri-i-butylsilyl, tri-n-hexylsilyl, dimethylethylsilyl, dimethyl-n-propylsilyl, dimethyl-n-butylsilyl, dimethyl-i-butylsilyl, dimethyl-tert-butylsilyl, dimethyl-n-pentylsilyl, dimethyl-n-octylsilyl, dimethylcyclohexylsilyl, dimethylhexylsilyl, dimethyl-2,3-dimethylpropylsilyl, dimethyl-2-(bicycloheptyl)silyl, dimethylbenzylsilyl, dimethylphenylsilyl, dimethyl-p-tolylsilyl, dimethylfrophemecylsilyl, methyldiphenylsilyl, triphenylsilyl, diphenyl-tert-butylsilyl, tribenzylsilyl, diphenylvinylsilyl, diphenyl-n-butylsilyl and phenylmethylvinylsilyl.

The carbon ring aliphatic group may, for example, be hexahydronaphthyl or tetrahydronaphthyl, which may be substituted by one or more members selected from $R^7$, $C_2$–$C_6$ acyloxy and hydroxy, preferably the following:

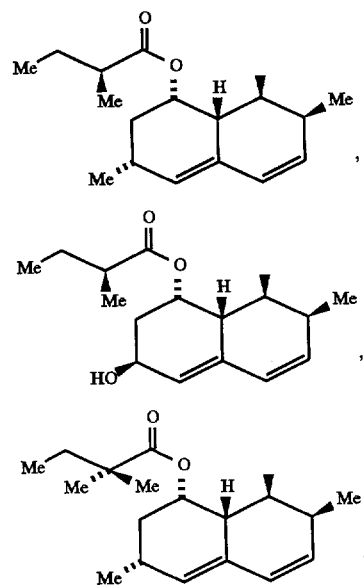

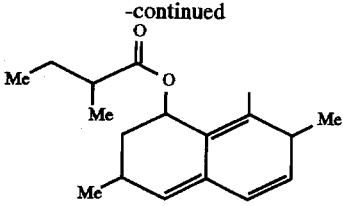

The carbon ring aromatic group may, for example, be phenyl or naphthyl, which may be substituted by from 1 to 3 members selected from $R^7$ and/or 1 or 2 substituents selected from $R^8$, preferably the following:

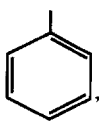

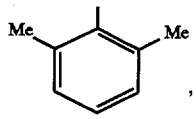

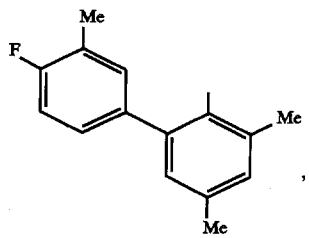

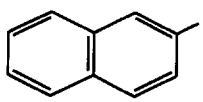

The heterocyclic aromatic group may, for example, be pyridyl, pyrimidinyl, pyrazolyl, imidazolyl, pyrrolyl, thienyl or furanyl, which may be substituted by from 1 to 3 members selected from $R^7$, $C_1$–$C_3$ alkoxymethyl, phenylcarbamoyl and/or 1 or 2 substituents selected from $R^8$, preferably the following:

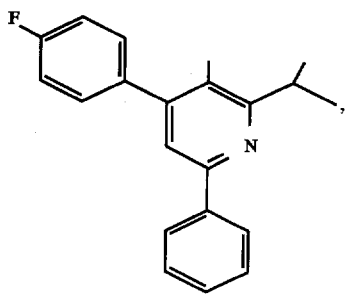

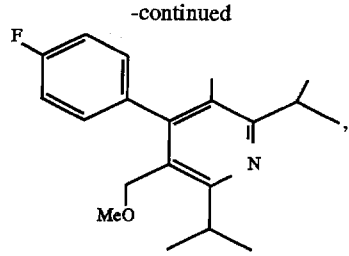

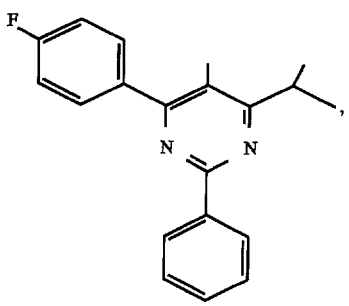

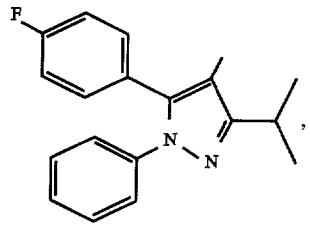

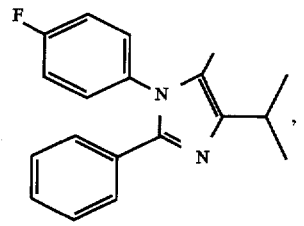

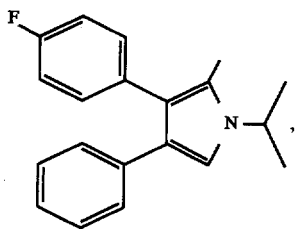

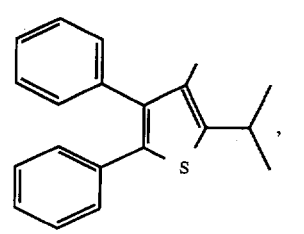

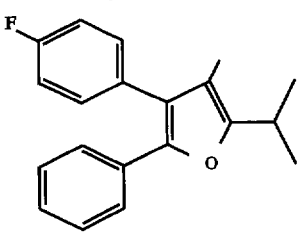

The condensed heterocyclic aromatic group may, for example, be indolyl, quinolyl, pyrazolopyridyl, thienopyridyl, pyrrolopyridyl or isoquinolinonyl, which may be substituted by from 1 to 3 members selected from $R^7$, $C_1$-$C_3$ alkoxymethyl, phenylcarbamoyl and/or 1 or 2 substituents selected from $R^8$, preferably the following:

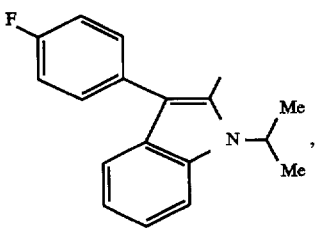

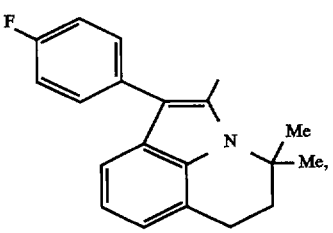

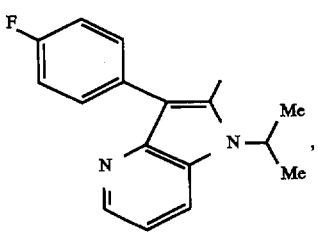

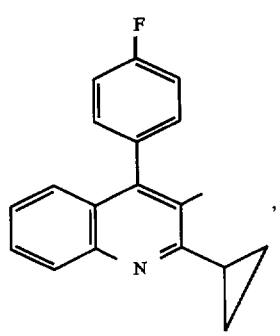

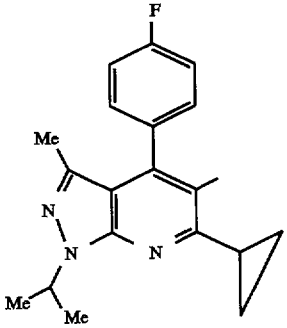

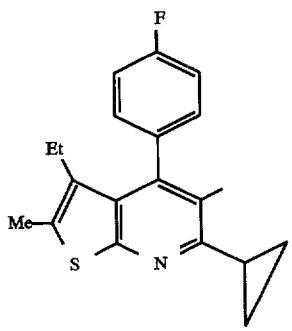

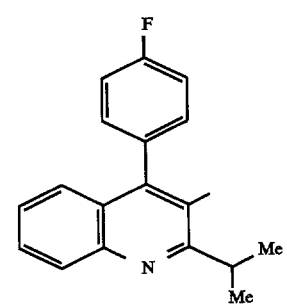

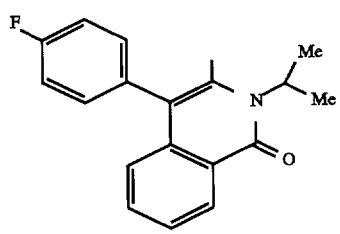

The chain unsaturated aliphatic group may, for example, be ethenyl or ethynyl, which may be substituted by one member selected from $R^7$, one or two members selected from $R^8$ and/or tetrazolyl, preferably the following:

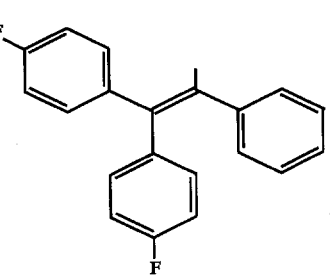

-continued

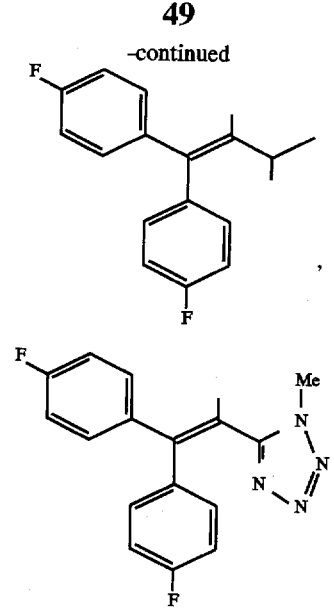

The cyclic unsaturated aliphatic group may, for example, be cyclohexenyl which may be substituted by from 1 to 4 members selected from $R^7$ and/or 1 or 2 substituents selected from $R^8$, preferably the following:

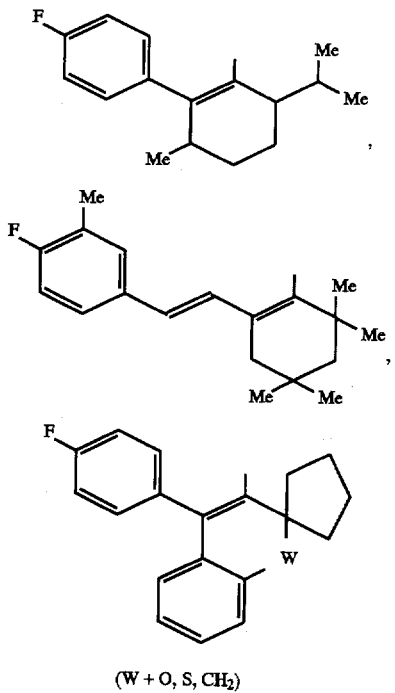

(W + O, S, $CH_2$)

Y and Z which are independent of each other, is —CO— or —CH(OH)—, provided that the two are not simultaneously —CH(OH)—.

$R^6$ is hydroxyl, $C_1-C_{10}$ alkoxy, a metal oxy group or a $C_0-C_7$ amino group.

$C_1-C_{10}$ alkoxy includes, for example, methoxy, ethoxy, n-propoxy, i-propoxy, n-butoxy, i-butoxy, sec-butoxy, tert-butoxy, n-pentoxy, n-hexyloxy, n-heptyloxy, n-octyloxy, n-nonyloxy, n-decanyloxy, cyclopropyloxy, cyclobutyloxy, cyclopentyloxy, cyclohexyloxy, cycloheptyloxy, cyclooctyloxy, cyclononyloxy, cyclodecanyloxy, 2-propenyloxy, cis-2-butenyloxy, trans-2-butenyloxy, β-methacryloxy, benzyloxy, o-methylbenzyloxy, m-methylbenzyloxy, p-methylbenzyloxy, phenoxy, o-methylphenoxy, m-methylphenoxy, p-methylphenoxy, 2,3-dimethylphenoxy, 2,4-dimethylphenoxy, 2,5-dimethylphenoxy, 2,6-dimethylphenoxy, 3,4-dimethylphenoxy, 3,5-dimethylphenoxy, α-naphthyloxy and β-naphthyloxy.

OM represents a carboxylate group, and M represents lithium, sodium, potassium, calcium or $NHR'_3$ (wherein R' is hydrogen, $C_1-C_3$ alkyl, $C_3-C_7$ cycloalkyl, $C_2-C_5$ alkenyl, phenyl or benzyl), preferably sodium, potassium, ammonium, trimethyl ammonium, triethyl ammonium, tri-n-propyl ammonium, tribenzyl ammonium, triphenyl ammonium, tricyclohexyl ammonium or trivinyl ammonium.

The $C_0-C_7$ amino group includes, for example, amino, methylamino, ethylamino, dimethylamino, n-propylamino, i-propylamino, methylamino, n-butylamino, i-butylamino, sec-butylamino, tert-butylamino, methyl-n-propylamino, methyl-i-propylamino, diethylamino, n-pentylamino, methyl-n-butylamino, methyl-i-butylamino, methyl-sec-butylamino, methyl-tert-butylamino, ethyl-n-propylamino, ethyl-i-propylamino, n-hexylamino, methyl-n-pentylamino, ethyl-n-butylamino, ethyl-i-butylamino, ethyl-sec-butylamino, ethyl-tert-butylamino, di-n-propylamino, n-propyl-i-propylamino, di-i-propylamino, cyclopropylamino, cyclobutylamino, cyclopentylamino, cyclohexylamino, dicyclohexylamino, N-methyl-N-phenylamino, α-methylbenzylamino, 1-adirydinyl, 1-azethinyl, 1-pyrrolydinyl, 1-piperidinyl and 1-pyrrolyl.

$R^7$ is $C_1-C_8$ alkyl or $C_3-C_7$ cycloalkyl. $C_1-C_8$ alkyl includes, for example, methyl, ethyl, n-propyl, i-propyl, n-butyl, i-butyl, sec-butyl, tert-butyl, n-pentyl, n-hexyl and n-heptyl. $C_3-C_7$ cycloalkyl includes, for example, cyclopropyl, cyclobutyl, cyclopentyl, cyclohexyl and cycloheptyl.

$R^8$ is phenyl which may be substituted by $C_1-C_7$ alkyl, fluoro, chloro or bromo, and it may, for example, be phenyl, 3-methylphenyl, 4-methylphenyl, 3,5-dimethylphenyl, 3-ethylphenyl, 4-ethylphenyl, 3,5-diethylphenyl, 3-methyl-5-ethylphenyl, 3-n-propylphenyl, 4-n-propylphenyl, 3,5-di-n-propylphenyl, 3-i-propylphenyl, 4-i-propylphenyl, 3,5-di-i-propylphenyl, 3-fluorophenyl, 4-fluorophenyl, 3,5-difluorophenyl, 3-chlorophenyl, 4-chlorophenyl, 3,5-dichlorophenyl, 3-fluoro-4-chlorophenyl, 3-bromophenyl, 4-bromophenyl or 3,5-dibromophenyl.

The solvent for this reaction may, for example, be an alcohol-type solvent such as methanol, ethanol, n-propanol or i-propanol, a polar solvent such as acetonitrile, dimethylformamide or dimethylsulfoxide, a halogen-type solvent such as dichloromethane, 1,1- or 1,2-dichloroethane, chloroform or carbon tetrachloride, or an ether-type solvent such as diethyl ether, di-n-propyl ether, tetrahydrofuran, 1,3- or 1,4-dioxane. Preferably, methanol, dichloromethane, diethyl ether or tetrahydrofuran is employed. More preferably, tetrahydrofuran is employed. The reaction can be conducted within a temperature range of from $-100°$ C. to $80°$ C., preferably from $-78°$ C. to $40°$ C., more preferably from $-10°$ C. to $30°$ C.

To conduct this reaction stoichiometrically, the β-aminoalkoxyborane complex (I) is used in an amount of from 1 to 2 equivalent to the carbonyl compound (III) or from 2 to 3 equivalent to the compound (V). On the other hand, to conduct this reaction catalytically, the β-aminoalcohol (II) is used in an amount of from 0.1 to 20 mol %, preferably from 1 to 10 mol %, and the borane reagent may, for example, be a borane.tetrahydrofuran complex, a borane.diethyl ether complex, a boraborane-pyridine complex, a borane.ammonia complex, a borane.tert-butylamine complex, a borane-N,N-diethylaniline complex, a borane-N,N-diisopropylethylamine complex, a borane-diethylamine complex, a borane.4-dimethylaminopyridine complex, a borane.4-ethylmorpholine complex, a borane.methylsulfide complex, a borane-trimethylamine complex, a borane.triphenylphosphine complex or a borane.triphenylphosphite complex. Preferably, a borane.tetrahydrofuran complex or a borane.diethyl ether complex is employed. More preferablly, a borane.tetrahydrofuran complex is employed. Further, to facilitate the catalytic reaction, an alcohol-type solvent such as methanol, ethanol, n-propanol or i-propanol, preferably methanol or ethanol, more preferably methanol, is preferably used in an amount within a range of from 3 to 10 equivalent, more preferably from 3 to 6 equivalent.

To improve the syn-selectivity in the asymmetric reduction reaction of a 1,3-dicarbonyl compound, a metal reagent such as a borane reagent, an aluminum reagent, a silicon reagent, a tin reagent, a phosphorus reagent, a titanium reagent, a zinc reagent, a magnesium reagent or a calcium reagent, may be used.

The borane reagent may, for example, be an alkoxyborane reagent such as diethylmethoxyborane, trimethoxyborane, tri-n-butoxyborane or catecholborane, a trialkylborane reagent such as triethylborane, triphenylborane, tri-n-butylborane, tri-sec-butylborane or tri-tert-butylborane, or a dialkylborane reagent such as cyamelborane or bicyclo [3.3.1]nona-9-borane (9-BBN).

The aluminum reagent may, for example, be an aluminum trialkoxide reagent such as aluminum tri-i-propoxide, aluminum triethoxide, aluminum tri-n-butoxide or aluminum tri-sec-butoxide, or an alkylaluminum alkoxide reagent such as diethylaluminum ethoxide, di-n-propylaluminum ethoxide or di-i-propylaluminum ethoxide.

The silicon reagent may, for example, be a tetralkoxysilane reagent such as tetramethoxysilane, tetraethoxysilane or tetraphenoxysilane, a trialkoxysilane reagent such as trimethoxy(methyl)silane, triethoxy(methyl)silane, trimethoxy(phenyl)silane, triethoxy(phenyl)silane, triethoxy (vinyl)silane or γ-chloropropyltrimethoxysilane, a dialkoxysilane reagent such as dimethoxydimethylsilane, diethoxydiethylsilane, dimethoxy(methyl)vinylsilane, diethoxy(methyl)silane, dimethoxy(ethyl)vinylsilane, diethoxy(methyl)vinylsilane, dimethoxydiphenylsilane or diethoxydiphenylsilane, a monoalkoxysilane reagent such as methoxytrimethylislane, ethoxytrimethylsilane, methoxy (dimethyl)vinylsilane or ethoxy(dimethyl)vinylsilane, or a dihydroxysilane reagent such as dihydroxydimethylsilane, dihydroxydimethylsilane, dihydroxydi-n-propylsilane, dihydroxydi-i-propylsilane or dihydroxydiphenylsilane.

The tin reagent may, for example, be an alkyl(tin) acetate reagent such as tri-n-butyltin acetate, di-n-butyltin diacetate or dioctyltin diacetate, or an alkyl(alkoxy)tin reagent such as dimethyldimethoxytin, diethyldimethoxytin, di-n-propyldimethoxytin, di-i-propyldimethoxytin, di-n-butyldimethoxytin, di-i-butyldimethoxytin, di-sec-butyldimethoxytin or di-tert-butyldimethoxytin.

The phosphorus reagent may, for example, be a triester of phosphorous acid such as trimethyl phosphite, triethyl phosphite, tri-i-propyl phosphite, tri-n-butyl phosphite or triphenyl phosphite.

The titanium reagent may, for example, be a titanium alkoxide such as tetraethyl orthotitanate, chlorotri-i-propyl orthotitanate, tetra-n-propyl orthotitanate, titanium tetra-i-propoxide or titanium tetra-n-butoxide.

The zinc reagent may, for example, be a zinc carboxylate such as zinc acetate, zinc propionate or zinc benzoate, a zinc halide such as zinc fluoride, zinc chloride, zinc bromide or zinc iodide, or an alkylzinc reagent such as dimethylzinc, diethylzinc, di-n-propylzinc or di-i-propylzinc.

The magnesium reagent may, for example, be a magnesium alkoxide reagent such as magnesium dimethoxide, magnesium diethoxide, magnesium di-n-propoxide or magnesium i-propoxide.

The calcium reagent may, for example, be a calcium alkoxide reagent such as calcium dimethoxide, calcium diethoxide, calcium di-n-propoxide or calcium i-propoxide.

Among these metal reagents, preferred are diethylmethoxyborane, aluminum tri-i-propoxide and trichlorotri-i-propyl orthotitanate, and more preferred are diethylmethoxyborane and aluminum tri-i-propoxide.

The metal reagent is used in an amount of from 1 to 3 equivalent, preferably from 1 to 1.2 equivalent, to the 1,3-dicarbonyl compound.

According to the present invention, the desired optically active 1,3-syn-diol compound of the formula (VI) can be synthesized in good yield and at a high syn-selectivity by reducing the 1,3-dicarbonyl compound of the formula (V) by a simple operation by means of the optically active β-aminoalkoxyborane complex of the formula (I). The optically active 1,3-syn-diol constitutes an important partial structure of an antihyperlipemia therapeutic agent (a HMG-CoA reductase inhibitor). Thus, the optically active β-aminoalkoxyborane complex (I) of the present invention is useful for the production of such a typical HMG-CoA reductase inhibitor as Lovastatin, Simvastatin or Pravastatin. Further, the compound of the present invention is applicable to various carbonyl compounds (of the formula (III)) to produce optically active alcohol compounds (of the formula (IV)) in good asymmetric yield.

Now, the present invention will. be described in further detail with reference to Examples. However, it should be understood that the present invention is by no means restricted to such specific Examples.

EXAMPLE 1

Preparation of the optically active β-aminoalcohol compound (II) (Steps A, B and D)

Preparation of (S)-N-(β-naphthyl)methyl-2-pyrrolidine methanol ((S)-II-1)

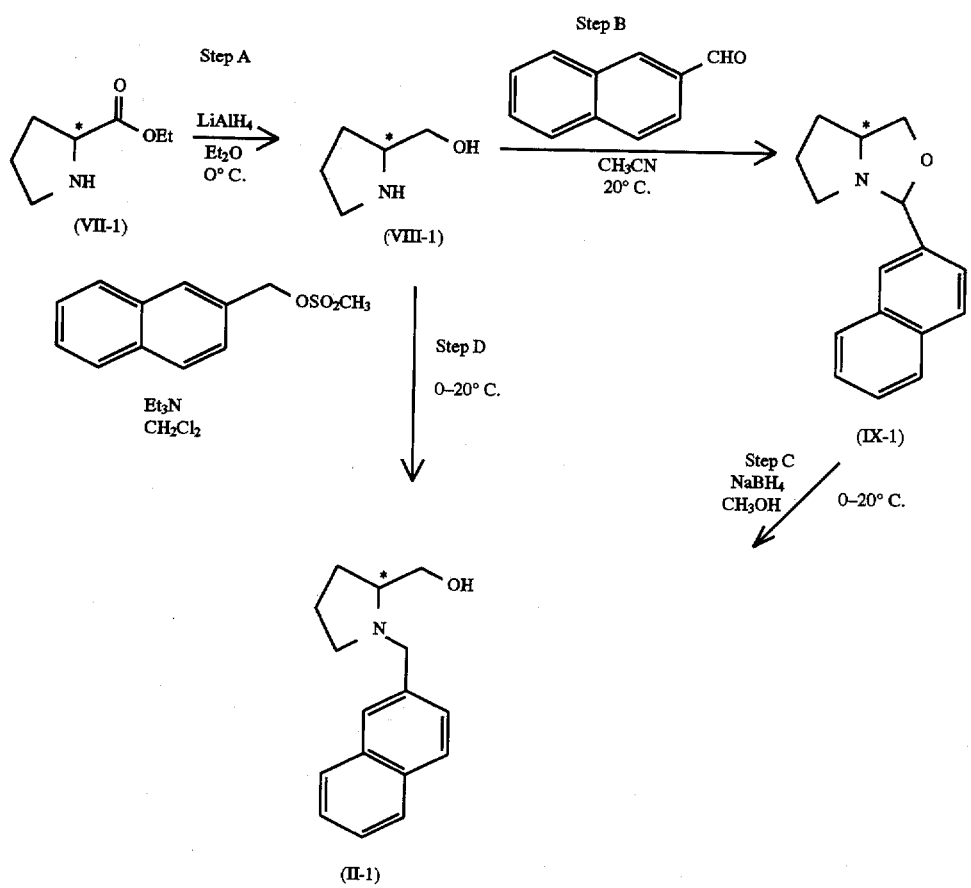

Step A

Commercially available proline ethyl ester (VII-1) was reduced in ethyl ether under cooling with ice by means of lithium aluminum hydride to obtain prolinol (VIII-1). Using optically active starting materials, the corresponding optically active prolinols (VIII-1) were obtained, respectively.

Steps B and C 1.000 g (9.89 mmol) of (S)-prolinol ((S)-(VIII-1) was dissolved in 25 ml of dry acetonitrile, and 1.545 g (9.89 mmol) of β-naphthoaldehyde was added thereto with stirring. The mixture was stirred for 24 hours. Then, acetonitrile was distilled off under reduced pressure to obtain an oxazolidine compound ((S)-(IX-1) (crude product: 2.55 g) quantitatively. Further, this oxazolidine compound was dissolved in 20 ml of methanol and cooled with ice. Then, 374 mg (9.89 mmol) of sodium borohydride was added thereto, and the mixture was stirred for 4 hours. Then, methanol was distilled off under reduced pressure, and the residue was recrystallized from chloroform to obtain S-N-(β-naphthyl) methyl-2-pyrrolidine methanol ((S)-II-1) (2.40 g) quantitatively.

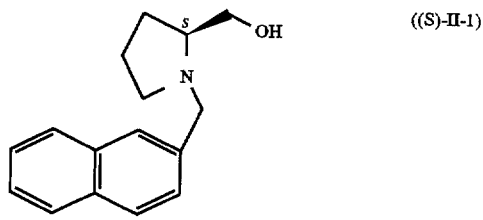

$[\alpha]_D^{20}$ −49.8° (C=0.1, $CH_3OH$)

IR spectrum (KBr)$\nu_{max}$ $cm^{-1}$:3200, 3030, 2950, 2850, 1600, 1580, 1420, 1 340, 1180, 1020, 850, 820, 740

$^1H$-NMR($CDCl_3$)δppm: 7.30–7.83(7H, m, aromatic-H), 2.28–4.23(8H, m, oth er-H), 1.66–1.90(4H, m, C—$CH_2$—$CH_2$—C)

Preparation of (R)-N-(β-naphthyl )methyl-2-pyrrolidine methanol ((R)-II-1)

Using (R)-prolinol ((R)-VIII-1) as the starting material, a similar operation was carried out to obtain R-N-(β-naphthyl) methyl-2-pyrrolidine methanol ((R)-II-1).

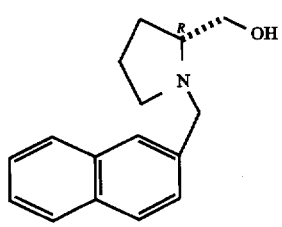

((R)-II-1)

$[\alpha]_D^{20}$+50.7° (C=0.1, CH$_3$OH)

IR spectrum (KBr)$v_{max}$ cm$^{-1}$:3200, 3030, 2950, 2850, 1600, 1580, 1420, 1 340, 1180, 1020, 850, 820, 740

$^1$H-NMR(COCl$_3$)δppm : 7.30–7. 83(7H, m, aromatic-H), 2.28–4.23(8H, m, other -H), 1.66–1.90 (4H, m, C—CH$_2$CH$_2$—C)

Preparation of (S)-N-(α-naphthyl)methyl-2-pyrrolidine methanol ((S)-II-2)

Using (S)-prolinol ((S)-VIII1) and α-naphthoaldehyde as the starting materials, a similar operation was carried out to obtain (S)-N-(α-naphthyl)methyl-2-pyrrolidine methanol ((S)-II-2).

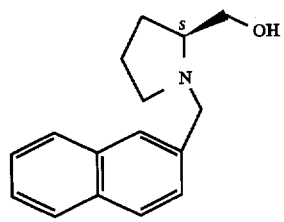

((S)-II-2)

$[\alpha]_D^{20}$–65.6° (C=0.16, CH$_3$OH)

IR spectrum(NaCl)$v_{max}$ cm$^{-1}$:3400, 3040, 2950, 2870, 1600, 1500, 1460, 1350, 1170, 1040, 800, 790, 780

$^1$H-NMR(CDCl$_3$)δppm:7.25–8.30(7H, m. aromatic-H), 2.60–4.55(7H, m, other -H), 2.35(1H. br, OH), 1.65–2.01 (4H, m. C—CH$_2$CH$_2$—C)

Preparation of (R)-N-(β-naphthyl)methyl-2-phenylqlycinol ((R)-II-3)

Using 1.00 g (7.29 mmol) of (R)-phenylglycinol ((R)-VIII-2) and β-naphthoaldehyde, a similar operation was carried out to obtain (R)-N-(β-naphthyl)methyl-2-phenylglycinol (2.01 g) ((R)-II-3) quantitatively.

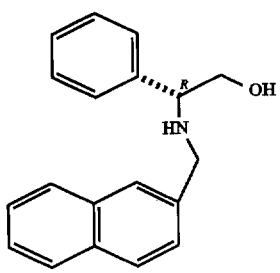

((R)-II-3)

$[\alpha]_D^{20}$+3.1° (C=0.1, CH$_3$OH)

$^1$H-NMR(CDCl$_3$)δppm:7.30–7.80(12H, m. aromatic-H), 3.50–4.30(5H, m, other -H), 2.30(1H. br, OH), 2.02(1H, m. br s, NH

EXAMPLE 2

Preparation of the optically active β-aminoalkoxyborane complex (i) (Step E)

Preparation of (S)-N-(β-naphthyl)methyl-2-pyrrolidine methoxyborane ((S)-I-1)

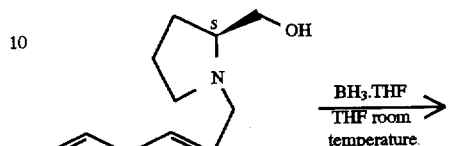

((S)-II-1)

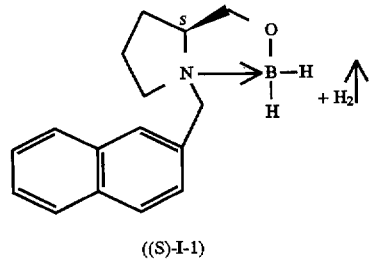

((S)-I-1)

2.41 g (10 mmol) of (S)-N-(p-naphthyl)methyl-2-pyrrolidine methanol ((S)-II-1) was dissolved in 50 ml of dry THF, and 10 ml of a tetrahydrofuran solution containing 1.0M of a borane-tetrahydrofuran complex (hereinafter referred to simply as a BH3.THF solution) was dropwise added thereto with stirring. After termination of generation of hydrogen gas, the mixture was further stirred for 10 minutes. This borane complex was used in the form of the THF solution for reduction of carbonyl compounds. Further, THF was distilled off at room temperature under reduced pressure to obtain 2.53 g (100%) of the desired substance as a viscous oily substance. The physical property values of this substance are as follows:

IR spectrum (KBR)$v_{max}$ cm$^{-1}$:3030, 2950, 2850, 2350(B-H), 1600, 1450 1420 1360, 1280, 1180, 1030, 850, 750

$^1$H-NMR(CDCl$_3$)δppm:7.30–7.83(7H, m. aromatic-H), 1.00–5.80(13H, m, other -H)

Using compounds ((R)-II-1), ((S)-II-2) and ((R)-II-3) as starting materials, similar operations were carried out to obtain optically active β-aminoalkoxyborane complexes (I) as identified in Table 2.

TABLE 2

| Structure | Chemical name |
|---|---|
| (structure shown) | (R)-[N-(β-naphthyl)methyl]-pyrrolidine methoxyborane [(R)-I-1] |

TABLE 2-continued

| Structure | Chemical name |
|---|---|
| (structure) | (S)-[N-(β-naphthyl)methyl]-pyrrolidine methoxyborane [(S)-I-2] |
| (structure) | (R)-[N-(β-naphthyl)methyl]-phenylethoxyborane [(R)-I-3] |

REFERENCE EXAMPLE 1

Preparation of ethyl (E) 7- [2'-cyclopropyl-4'-(p-fluorophenyl)quinolin- 3'-yl]-3,5-dioxo-6-heptenoate Under a nitrogen stream, 2.35 g (63.1 mmol) of 60% sodium hydride was suspended in 300 ml of dry THF, and the suspension was stirred for 5 minutes and then cooled with ice. Then, 7.47 g (57.4 mmol) of ethyl acetoacetonate was gradually dropwise added by an injector, and after termination of generation of hydrogen, the mixture was stirred for 15 minutes. Then, 37.8 ml (60.3 mmol) of 1.6M n-butyl lithium was gradually dropwise added thereto by an injector, and the mixture was stirred for 15 minutes. After confirming that the color of the reaction solution turned to yellow to orange red, 6.00 g (15.9 mmol) of (E)3-[240-cyclopropyl-4'-(p-fluorophenyl)quinolin-3'-yl]-2-propenoic acid-N-methyl-N-methoxyamide (G. B. Reddy, T. Minami, T. Hanamoto, T. Hiyama, J. Org. Chem., 56, 5754, 1991) was dissolved in 100 ml of dry THF, and the solution was dropwise added to the reaction solution. Then, the reaction temperature was raised to room temperature, and the mixture was stirred for 24 hours. The reaction solution was cooled with ice, and the reaction was terminated by an addition of 200 ml of a 1M acetic acid aqueous solution. The aqueous layer was separated and extracted twice with 200 ml of ethyl acetate. The extract was put into the organic layer, and the mixture was washed twice with 50 ml of a saturated sodium chloride aqueous solution and dried over anhydrous magnesium sulfate. Then, the solvent was distilled off under reduced pressure, and the residue was purified by silica gel column chromatography (developing solvent: hexane/ethyl acetate=10/1) and then recrystallized from ethyl acetate to obtain 3.11 g of the above-identified compound.

MS spectrum(eI)m/e: 445(M⁻), 400, 358, 330, 316, 288

$^1$H-NMR(CDCl$_3$)δppm :7.97–7.19(8H, m, aromalic-H), 7.71(1H, d, J=16 Hz, COCH=), 6.03(1H, d, J=16 Hz, COC=CH), 5.51(1H, s, enol-olefinic-H), 4.21 (2H, q, J=7 Hz, COOCH$_2$), 3.40(2H, s, COCH$_2$COO), 2.35–2.40(1H, m, CH-c-propyl), 1.39–1.41, 1.07–1.09(4H, m, —CH$_2$CH$_2$—), 1.28(3H, t,J=7 Hz, COOCCH$_3$)

EXAMPLE 3

Catalytic asymmetric reduction of a monocarbonyl compound by means of the optically active N-naphthylmethyl-2-pyrrolidine methanol (compound (II)/BH$_3$)

A carbonyl compound (1 mmol) was dissolved in 5 ml of THF, and 192 mg (6 mmol) of methanol and 23 mg (0.1 mmol) of the optically active N-naphthylmethyl-2-pyrrolidine methanol (compound (II)) were added thereto. Then, 3 ml or 10 ml (3 mmol or 10 mmol) of a 1M BH$_3$.THF solution was added thereto, and the mixture was stirred under a temperature condition of 20° C. or 30° C. for from 6 to 19 hours. To the reaction solution, 13 ml of 1N HCl was added for salting out, followed by extraction with 100 ml of ethyl acetate. Then, the extract was washed with 10 ml of a saturated sodium chloride aqueous solution and dried over anhydrous magnesium sulfate. Then, the solvent was distilled off under reduced pressure, and the obtained liquid was purified by a thin layer chromatography for separation to obtain the desired optically active alcohol quantitatively.

Table 3 shows the results of asymmetric reduction of various monocarbonyl compounds using the optically active N-naphthylmethyl-2-pyrrolidine methanol (compound (II-1) or compound (II-2)). The asymmetric yield and the absolute configuration of the obtained alcohol were determined by comparison with an optically active standard product by converting the alcohol product to a urethane diastereomer, followed by high performance liquid chromatography using silica gel in accordance with a high performance liquid chromatography analysis using a CHIRALCEL OD column by Daicel Chemical Industries, Ltd. or the method by Lamed et al. (E. Keinan, E. K. Hafeli, K. K. Seth, and R. Lamed, J. Am. Chem. Soc., 108, 162 (1986)).

TABLE 3

[II-1] β-napthyl form
[II-2] α-napthyl form $$R^3\text{-CO-}R^4 \xrightarrow[\text{THF}]{\text{BH}_3\cdot\text{THF}} R^3\text{-CH(OH)-}R^4$$
(III) → (IV)

(with chiral catalyst: HO-CH₂-pyrrolidine-N-CH₂-naphthyl)

| Test No. | Carbonyl compound | Compound (II) (mol times) | Chemical yield (%) | Asymmetric yield (%) | Absolute configuration |
|---|---|---|---|---|---|
| 1 | Ph-COMe | [(S)-II-1] 0.1 | 94<sup>a)</sup> | 100 | S |
| 2 | Ph-COMe | [(S)-II-2] 0.1 | 91<sup>a)</sup> | 100 | S |
| 3 | α-tetralone | [(S)-II-2] 0.1 | 94<sup>a)</sup> | 70 | — |
| 4 | 2-hexanone | [(S)-II-1] 0.002 | 100<sup>b)</sup> | 46 | R |
| 5 | 2-hexanone | [(S)-II-1] 0.02 | 100<sup>b)</sup> | 99 | R |
| 6 | 2-hexanone | [(S)-II-1] 0.05 | 100<sup>b)</sup> | 99 | R |
| 7 | 2-hexanone | [(S)-II-1] 0.2 | 100<sup>b)</sup> | 99 | R |

<sup>a)</sup>Reaction temp.: 30° C., Reaction time: 6 hrs, BH₃.THF: 10 mmol
<sup>b)</sup>Reaction temp.: 20° C., Reaction time: 19 hrs, BH₃.THF: 3 mmol The compound (I) of the present invention presented a high asymmetric yield in a catalytic amount in the asymmetric reduction of a monocarbonyl compound (III), without isolation i.e. as formed in the reaction system by the compound (II), in the case of conventional asymmetric reduction using 2-hexanone as the substrate (J. Chem. Soc. Perkin Trans. I. 2887 (1984), J. Org. Chem. 49, 555 (1984)), even when a borane complex was used in a stoichiometric amount, the asymmetric yield was only 25% ee (a borane complex having a polymer substituent introduced on the nitrogen of (S)-proline) or 55% ee (a (S)-2-amino-3-methyl-1,1-diphenylbutan-1-ol borane complex). Thus, the superiority of the compound of the present invention was proved.

EXAMPLE 4

Asymmetric reduction of a 1,3-dicarbonyl compound (V) by various optically active β-aminoalkoxyborane complexes (I)

1 mmol (445.5 mg) of a 1,3-dicarbonyl compound (V) was dissolved in 30 ml of THF, and 1 ml of a THF solution of 1.0M diethylmethoxyborane.THF or 1 mmol (204.3 mg) of aluminum tri-i-propoxide was added thereto with stirring. The mixture was adjusted to −78° C. or 20° C. under a nitrogen gas stream.

To this 1,3-dicarbonyl compound (V) solution, the (S)-N-(β-naphthyl)methyl-2-pyrrolidine methoxyborane complex ((S)-I-1) obtained in Example 2 was dropwise added, and the mixture was stirred for 3 hours. Otherwise, to form the borane complex in the reaction system, from 2 to 10 ml (2 to 10 mmol) of a 1.0M BH₃.THF solution was dropwise added to the (S)-N-(β-naphthyl)methyl-2-pyrrolidine methanol ((S)-I-1) obtained in Example 1 or a THF solution of various optically active β-aminoalcohol (0.1 to 3 mmol). This solution is dropwise added to the above 1,3-dicarbonyl compound (V), and the mixture was stirred for from 3 to 28 hours. In the case where a catalytic amount of β-aminoalcohol is employed, 192 mg (6 mmol) of methanol was further added.

Then, acetic acid (9 mmol, 540.5 mg) was added to the reaction solution, and the mixture was diluted with 300 ml of ethyl acetate, washed with 20 ml of a saturated sodium chloride aqueous solution and dried over anhydrous sodium sulfate. The solvent was distilled off under reduced pressure, and 1 l of methanol was added to the orange red liquid thereby obtained, and the mixture was heated at a temperature of from 50° to 60° C. for one hour. Then, methanol was distilled off under reduced pressure. The obtained yellow liquid was purified by silica gel column chromatography to obtain the desired optically active 1,3-syn-diol compound (VI-1). The determination of the asymmetric yield (% ee) was conducted by high performance liquid chromatography using CHIRALCEL OD column, manufactured by Daicel Chemical Industries, Ltd.

With respect to the reducing agents shown in Table 4, the β-aminoalkoxyborane complex ((S)-I-1) was used in Test Nos. 1 to 3. In Test Nos. 4 to 9, the β-aminoalkoxyborane complex formed in the reaction system by β-aminoalcohol, was used. In Test No. 5 and 6, a catalytic amount of β-aminoalcohol ((S)-II-1) was used. Further, in Test No. 6, dichloromethane was used as the solvent.

TABLE 4

| No. | Reducing agent | Metal reagent | Chemical yield (%) | syn-forming rate (%) (syn/syn + anti) | Asymmetric yield (% ee) | Absolute configuration |
|---|---|---|---|---|---|---|
| 1 | [(S)-I-1] 3 molar times | Et$_2$BOMe | 42[a] | 99 | 100 | 3S, 5R |
| 2 | [(S)-I-1] 3 molar times | Et$_2$BOMe | 53[a] | 94 | 100 | 3S, 5R |
| 3 | [(S)-I-1] 3 molar times | — | 51[a] | 95 | 100 | 3S, 5R |
| 4 | [(S)-II-1] + BH$_3$ 3 molar times each | Et$_2$BOMe | 50[b] | 95 | 100 | 3S, 5R |
| 5 | [(S)-II-1] 0.1 molar time + BH$_3$ 10 molar times | Et$_2$BOMe | 33[c] | 94 | 91 | 3S, 5R |
| 6 | [(S)-II-1] 0.25 molar time + BH$_3$ 10 molar times | Et$_2$BOMe | 13[d] | 95 | 94 | 3S, 5R |
| 7 | [(R)-II-1] + BH$_3$ 2 molar times each | Et$_2$BOMe | 19[e] | 100 | 24 | 3R, 5S |
| 8 | [(R)-II-1] + BH$_3$ 2 molar times each | Al(OPr-i)$_3$ | 15[e] | 99 | 100 | 3R, 5S |
| 9 | [(R)-II-1] + BH$_3$ 3 molar times each | Al(OPr-i)$_3$ | 74[f] | 99 | 100 | 3R, 5S |

[a] Reaction temp.: −78° C., Reaction time: 3 hrs
[b] Reaction temp.: 20° C., Reaction time: 3 hrs
[c] Reaction temp.: 20° C., Reaction time: 28 hrs
[d] Reaction temp.: −78° C., Reaction time: 23 hrs, CH$_2$Cl$_2$ solvent
[e] Reaction temp.: −78° C., Reaction time: 5 hrs
[f] Reaction temp.: 20° C., Reaction time: 20 hrs

COMPARATIVE EXAMPLE 1

Using conventional borane complexes, the operation was conducted in the same manner as in Example 4. The results are shown in Table 5.

TABLE 5

(V-1) [H]*/THF → (VI-1)

| Test No. | Reducing agent | Borane reagent Et₂BOMe | Chemical yield (%) | syn-forming rate (%) (syn/syn + anti) | Asymmetric yield (% ee) | Absolute configuration |
|---|---|---|---|---|---|---|
| 1 | (structure, 2 molar times) | — | 78[a] | 60 | 21 | 3S, 5R |
| 2 | (structure, 3 molar times) | 1 eq | 65[a] | 82 | 23 | 3S, 5R |
| 3 | (structure with CH₃, 3 molar times) | 1 eq | 68[a] | 43 | 14 | 3S, 5R |
| 4 | (structure with benzyl, 3 molar times) | 1 eq | 28[b] | 38 | 6 | 3S, 5R |

[a]Reaction temp.: −78° C., Reaction time: 3 hrs
[b]Reaction temp.: 20° C., Reaction time: 3 hrs

EXAMPLE 5

50 mg (0.27 mmol) of ethyl 3,5-dioxo-6-heptynoate was dissolved in 5 ml of THF and 52 ml of methanol. Then, with or without addition of aluminum tri-i-propoxide as a metal reagent, a reaction was conducted at 20° C. for 20 hours using 5.4 ml of a 1.0M BH₃.THF solution and 6.2 mg (0.027 mmol) of the (S)-N-(β-naphthyl)methyl-2-pyrrolidine methanol (compound (S)-II-1) obtained in Example 1, to obtain ethyl 3,5-dihydroxy-6-heptynoate (VI-2) as oily desired product.

$^1$H-NMR(COCl₃)δppm: 4.81(1H, br, ≡—CH—OH), 4.17(2H, q, J=7 Hz, COOCH₂), 3.60(1H, m, C—C H(OH)—C), 3.04(1H, s, C≡C-H), 1.50–1.65(6H, m, other-H), 1.3(3H, t, J=7 Hz, COOCH₂CH₃).

IR(NaCl) cm$^{-1}$:3400(OH), 2220(C≡C), 1720(C=O).

TABLE 6

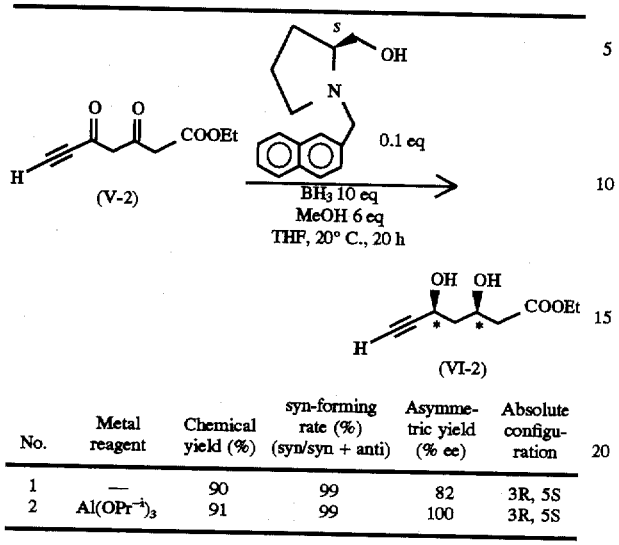

| No. | Metal reagent | Chemical yield (%) | syn-forming rate (%) (syn/syn + anti) | Asymmetric yield (% ee) | Absolute configuration |
|---|---|---|---|---|---|
| 1 | — | 90 | 99 | 82 | 3R, 5S |
| 2 | Al(OPr$^{-i}$)$_3$ | 91 | 99 | 100 | 3R, 5S |

The compound of the present invention presented a higher asymmetric yield and a higher diastereo-selectivity (higher syn-formation rate) than conventional borane complex catalysts, in a catalytic amount, in the asymmetric reduction of 1,3-dicarbonyl compounds (V-1) and (V-2).

We claim:

1. An optically active β-aminoalkoxyborane complex of the formula (I):

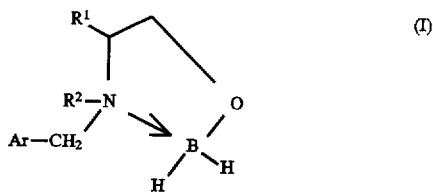

(I)

wherein $R^1$ is $C_1$–$C_8$ alkyl, $C_3$–$C_7$ cycloalkyl, $C_7$–$C_{11}$ aralkyl or $C_6$–$C_{10}$ aryl, $R^2$ is hydrogen, $C_1$–$C_8$ alkyl $C_3$–$C_7$ cycloalkyl or $C_7$–$C_{11}$ aralkyl, or $R^1$ and $R^2$ together form $(CH_2)_n$ wherein n is 3 or 4, and Ar is naphthyl, anthryl or phenanthryl, which may be substituted by from 1 to 3 substituents selected from the group consisting of halogen, nitro, $C_1$–$C_6$ alkyl, $C_3$–$C_7$ cycloalkyl, $C_2$–$C_6$ alkenyl, $C_2$–$C_6$ alkynyl, $C_7$–$C_{11}$ aralkyl, $C_6$–$C_{10}$ aryl, $C_1$–$C_6$ alkoxy and styrene polymer substituents.

* * * * *